US012558134B2

(12) United States Patent
Rakes et al.

(10) Patent No.: US 12,558,134 B2
(45) Date of Patent: Feb. 24, 2026

(54) PERIPROSTHETIC BONE PLATE SYSTEMS

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Jordan Rakes, Cordova, TN (US); Adam Zysk, Germantown, TN (US); Nicholas S. Ritchey, Collierville, TN (US); Charles R. Bennett, Memphis, TN (US); Kohsuke Watanabe, Memphis, TN (US); Paul Tornetta, Brookline, MA (US); William Ricci, New York, NY (US); Reza Firoozabadi, Mercer Island, WA (US); John Tracy Watson, Paradise Valley, AZ (US); Samir Mehta, Haddonfield, NJ (US); Brian McGrory, Falmouth, ME (US); George Babikian, Freeport, ME (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 742 days.

(21) Appl. No.: 17/772,319

(22) PCT Filed: Oct. 29, 2020

(86) PCT No.: PCT/US2020/057829
§ 371 (c)(1),
(2) Date: Apr. 27, 2022

(87) PCT Pub. No.: WO2021/087024
PCT Pub. Date: May 6, 2021

(65) Prior Publication Data
US 2022/0395303 A1      Dec. 15, 2022

Related U.S. Application Data
(60) Provisional application No. 62/927,478, filed on Oct. 29, 2019.

(51) Int. Cl.
*A61B 17/80*          (2006.01)
(52) U.S. Cl.
CPC ...... *A61B 17/8014* (2013.01); *A61B 17/8047* (2013.01); *A61B 17/8057* (2013.01)
(58) Field of Classification Search
CPC ............ A61B 17/8014; A61B 17/8057; A61B 17/8061
See application file for complete search history.

(56) References Cited

U.S. PATENT DOCUMENTS 6,623,486 B1    9/2003   Weaver et al.
7,207,993 B1    4/2007   Baldwin et al.
(Continued)

FOREIGN PATENT DOCUMENTS

CN      108056808 A    5/2018
EP        3542739 A1    9/2019
(Continued)

OTHER PUBLICATIONS

US 9,597,139 B2, 03/2017, Cavallazzi (withdrawn)
(Continued)

*Primary Examiner* — Nicholas W Woodall
(74) *Attorney, Agent, or Firm* — KDW Firm PLLC

(57)          ABSTRACT
Periprosthetic bone fixation plates are disclosed including, for example, periprosthetic proximal femur plate, periprosthetic distal femur plate, periprosthetic humerus plate,
(Continued)

periprosthetic ring plate, and periprosthetic troch plate. In use, the periprosthetic bone fixation plates are arranged and configured for use in periprosthetic fractures. That is, the periprosthetic plates include one or more features to facilitate positioning and securement of the bone fixation plate to a patients bone that previously received a surgically implanted orthopedic device or implant such as, for example, an intramedullary nail, a hip prosthesis, a knee prosthesis, etc. In use, the one or more features are designed and configured to facilitate avoidance of the previous surgically implanted orthopedic device or implant. In addition, the periprosthetic bone fixation plates are arranged and configured to facilitate plating of a longer working length as compared to existing bone fixation plates (e.g., plating from, for example, femoral condyle to greater trochanter).

15 Claims, 13 Drawing Sheets

(56)                    References Cited

U.S. PATENT DOCUMENTS

| | | | |
|---|---|---|---|
| 7,341,589 B2 | 3/2008 | Weaver | |
| 7,695,472 B2 * | 4/2010 | Young | A61B 17/8052 |
| | | | 606/291 |
| 8,328,809 B2 | 12/2012 | Wenk et al. | |
| 8,668,692 B1 | 3/2014 | Lindvall | |
| 8,709,092 B2 | 4/2014 | Segina et al. | |
| 8,728,168 B2 | 5/2014 | Hanssen et al. | |
| 8,808,333 B2 | 8/2014 | Kuster et al. | |
| 8,961,517 B2 | 2/2015 | McClintock | |
| 9,131,968 B2 | 9/2015 | Cavallazzi et al. | |
| 9,138,244 B2 | 9/2015 | Mebarak et al. | |
| 9,138,267 B2 | 9/2015 | Cavallazzi | |
| 9,138,268 B2 | 9/2015 | Cavallazzi et al. | |
| 9,138,269 B2 | 9/2015 | Cavallazzi et al. | |
| 9,155,575 B2 | 10/2015 | Wenk et al. | |
| 9,211,151 B2 | 12/2015 | Weaver et al. | |
| 9,326,807 B2 | 5/2016 | Schaller et al. | |
| 9,345,523 B2 | 5/2016 | Segina et al. | |
| 9,463,053 B2 | 10/2016 | Garino | |
| 9,486,261 B2 | 11/2016 | Plecko et al. | |
| 9,504,503 B2 | 11/2016 | Cavallazzi et al. | |
| 9,522,066 B2 | 12/2016 | Segina et al. | |
| 9,668,794 B2 | 6/2017 | Kuster et al. | |
| 9,687,282 B2 * | 6/2017 | Strnad | A61B 17/8047 |
| 9,707,025 B2 | 7/2017 | Cavallazzi | |
| 10,092,337 B2 | 10/2018 | Austin et al. | |
| 11,096,730 B2 * | 8/2021 | Tiongson | A61B 17/8057 |
| 2004/0059334 A1 | 3/2004 | Weaver | |
| 2004/0225291 A1 | 11/2004 | Schwammberger | |
| 2008/0300637 A1 | 12/2008 | Austin et al. | |
| 2010/0262194 A1 | 10/2010 | Wagner et al. | |
| 2012/0323284 A1 | 12/2012 | Baker et al. | |
| 2013/0013078 A1 | 1/2013 | Hanssen et al. | |
| 2013/0013080 A1 | 1/2013 | Hanssen et al. | |
| 2013/0211463 A1 | 8/2013 | Mizuno et al. | |
| 2013/0238032 A1 * | 9/2013 | Schilter | A61B 17/846 |
| | | | 606/281 |
| 2014/0128873 A1 | 5/2014 | McClintock | |
| 2014/0243907 A1 | 8/2014 | Cavallazzi et al. | |
| 2015/0051651 A1 * | 2/2015 | Terrill | A61B 17/8052 |
| | | | 606/289 |
| 2015/0257802 A1 | 9/2015 | Wolf et al. | |
| 2015/0282935 A1 | 10/2015 | Kuldjanov et al. | |
| 2016/0095636 A1 | 4/2016 | Wiederkehr | |
| 2016/0338748 A1 | 11/2016 | Champagne | |
| 2016/0374739 A1 | 12/2016 | Garino | |
| 2017/0035476 A1 | 2/2017 | Cavallazzi et al. | |
| 2017/0056081 A1 | 3/2017 | Langdale et al. | |
| 2017/0151059 A1 | 6/2017 | Segina et al. | |
| 2018/0256220 A1 * | 9/2018 | Koay | A61B 17/8061 |
| 2018/0256226 A1 * | 9/2018 | Govey | A61B 17/8085 |
| 2019/0046250 A1 | 2/2019 | Sylvestre | |
| 2019/0076174 A1 | 3/2019 | Tiongson et al. | |
| 2019/0290338 A1 | 9/2019 | Bosshard et al. | |
| 2019/0365437 A1 | 12/2019 | Lueth | |

FOREIGN PATENT DOCUMENTS

| | | | |
|---|---|---|---|
| WO | 2020247381 A1 | 12/2020 | |
| WO | 2021087024 A1 | 5/2021 | |

OTHER PUBLICATIONS

International Search Report and Written Opinion for PCT/US2020/057829, mailed Mar. 3, 2021.

DePuy Synthes; Periprosthetic Implants. Product Overview, dated Oct. 2013.

Fracture After Total Hip Replacement—OrthoInfo—AAOS https://orthoinfo.aaos.org/en/diseases-conditions/fractrue-after-total-hip-replacement, dated May 2018.

Zimmer; NCB(R) Periprosthetic Femur Plate System—Surgical Technique, dated May 2015.

China Patent Office, First Office Action with translation, dated May 26, 2025; 18 pages.

* cited by examiner

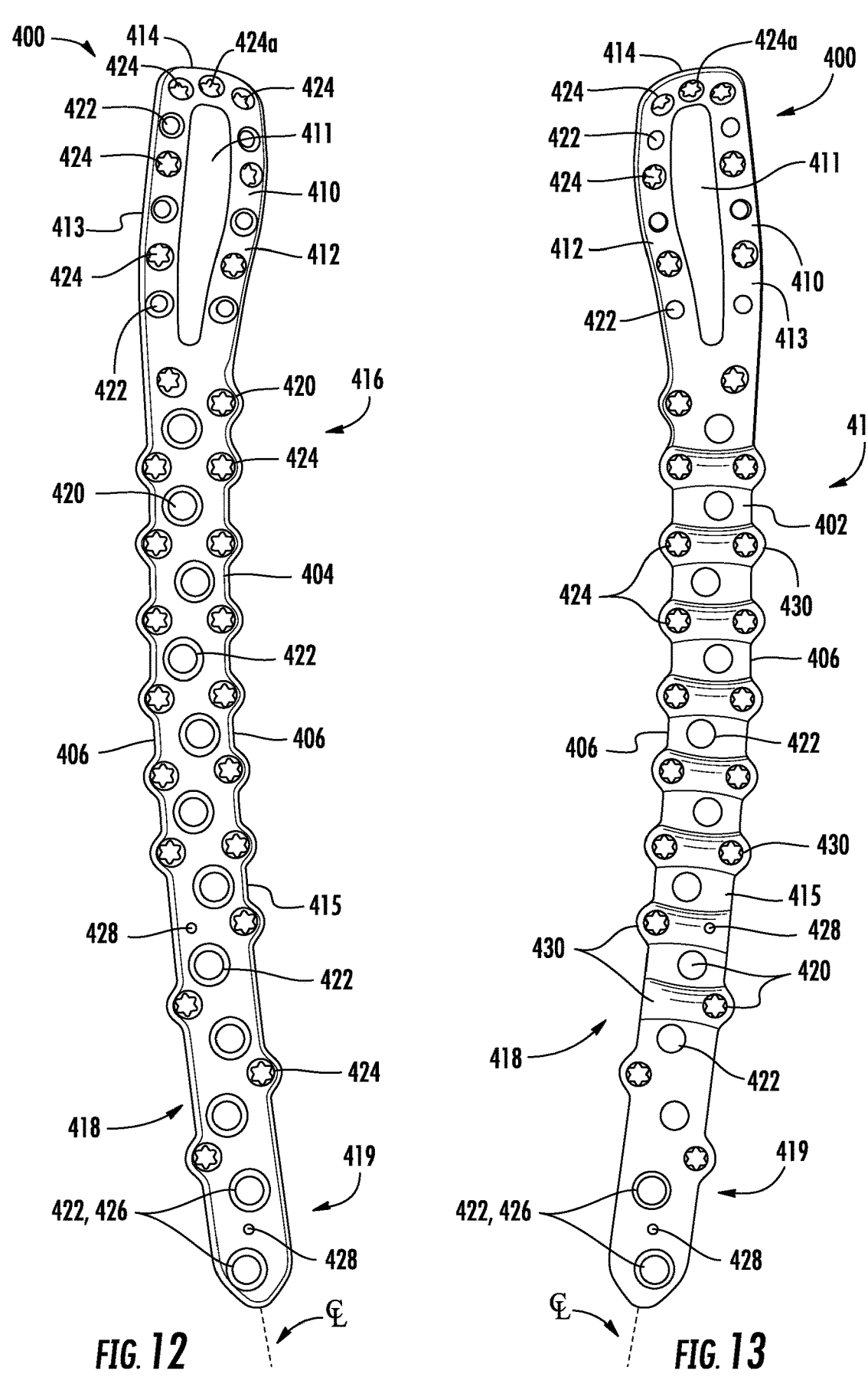
*FIG. 12*                              *FIG. 13*

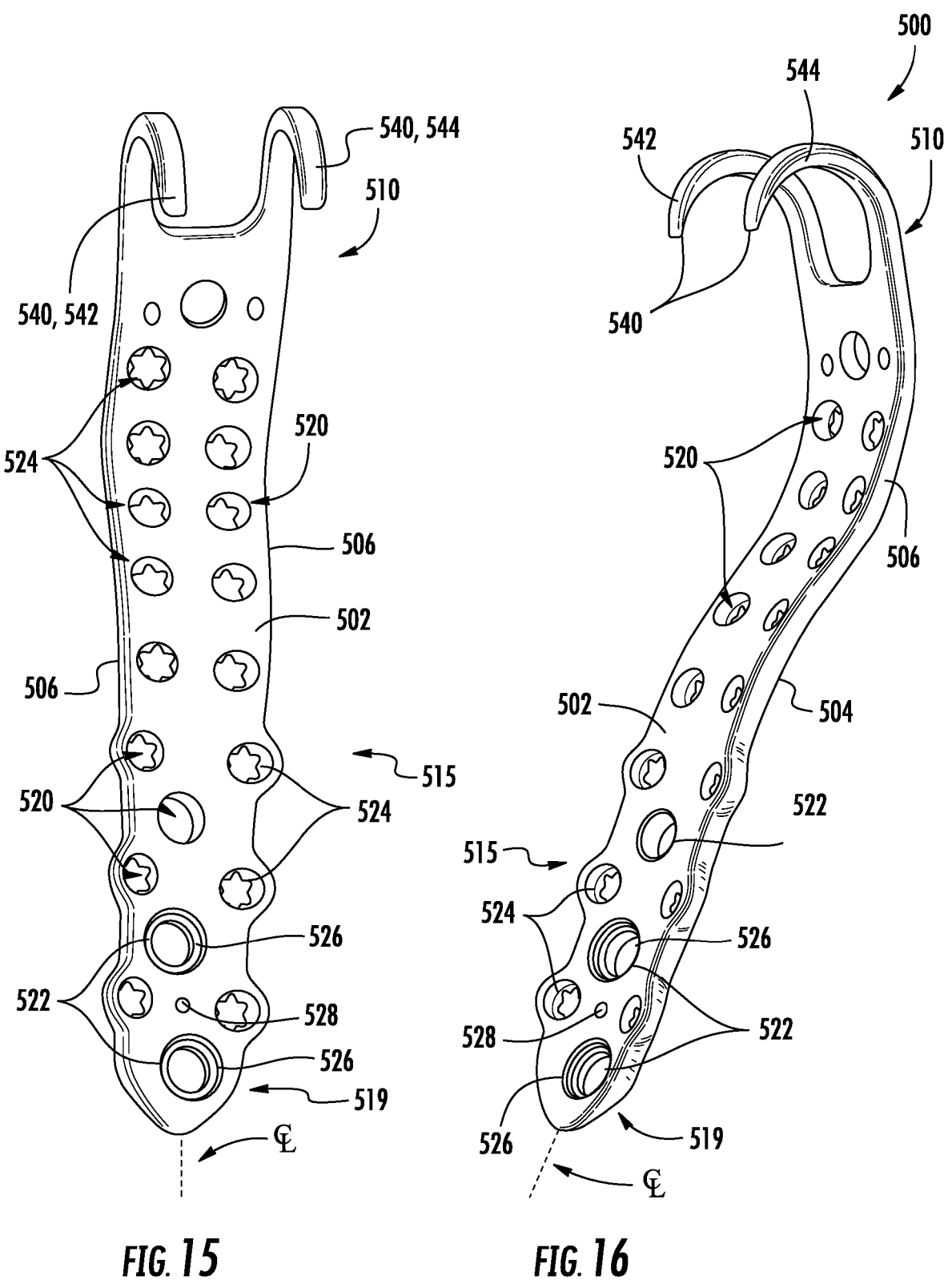
*FIG. 15*            *FIG. 16*

PERIPROSTHETIC BONE PLATE SYSTEMS

CROSS-REFERENCE TO RELATED APPLICATIONS

This application is a National Phase filing of International Application No. PCT/US2020/057829, filed Oct. 29, 2020, which application is a non-provisional of, and claims the benefit of the filing date of, U.S. provisional patent application No. 62/927,478, filed Oct. 29, 2019, entitled "Periprosthetic Bone Plate Systems" the entirety of each application is incorporated by reference herein.

TECHNICAL FIELD

The present disclosure is directed to orthopedic implants for coupling to one or more patient's bones, bone portions, bone fragments, etc., and more specifically to bone plate systems for facilitating stabilization of periprosthetic fractures.

BACKGROUND

Bone fractures are often repaired by securing an orthopedic implant or device to one or more patient's bone(s), bone portions, bone fragments, etc. (used interchangeably without the intent to limit). For example, it is not uncommon for a patient to receive an orthopedic knee prosthesis, an orthopedic hip prosthesis, an intramedullary ("IM") nail, etc. to repair one or more factures in a patient's bone.

On occasion a bone fracture may occur in the area surrounding a previous surgically implanted orthopedic implant or device. For example, a fracture may occur during a surgical implant procedure. Alternatively, however, as is the case in most scenarios, a periprosthetic fracture may occur in a patient years after the original surgical implant procedure. In some cases, a surgically implanted orthopedic implant may predispose a patient's bone to later fractures.

Whatever the cause, periprosthetic fractures surrounding a previous surgically implanted orthopedic implant pose unique fixation challenges. For example, the previous surgically implanted orthopedic device or implant may interfere with the placement of a subsequently implanted orthopedic bone fixation plate.

For example, in one scenario, a periprosthetic hip fracture may occur adjacent or around a previous surgically implanted hip replacement prosthesis. As the number of hip replacement prosthesis has increased, so too has the number of periprosthetic fractures associated therewith. Once a fracture occurs in the area surrounding a previous surgically implanted hip replacement prosthesis, treatment may be complicated by osteoporosis, defects in the bone, and the presence of the previous surgically implanted hip replacement prosthesis. For example, stems, rods, screws, and cement associated with the previous surgically implanted hip replacement prosthesis may block the patient's medullary canal, preventing intramedullary fixation of the subsequent fracture. Moreover, stems and rods may also block screw fixation through the medullary canal to secure a subsequent bone plate to the patient's bone. As a result, periprosthetic factures and the corresponding techniques for treating periprosthetic fractures are generally more difficult, with limited options.

Nevertheless, periprosthetic fractures require treatment. For example, an unstable periprosthetic fracture may require surgical stabilization and/or implant replacement to restore function. Surgical stabilization may include implantation of a bone fixation plate to secure the adjacent sections of the fractured bone to facilitate healing, which may occur with or without implant replacement.

Many currently known bone fixation plates are not designed with periprosthetic fractures in mind, as a result they often exhibit one or more shortcomings or disadvantages. It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is a number of bone fixation plates (e.g., periprosthetic bone plates). The bone fixation plates are arranged and configured for use in periprosthetic fractures. For example, in one embodiment, the bone fixation plate may be in the form of a proximal femur plate for use in a periprosthetic fracture surrounding, for example, a hip replacement prosthesis. Alternatively, in one embodiment, the bone fixation plate may be in the form of a distal femur plate for use in a periprosthetic fracture surrounding, for example, a knee replacement prosthesis. In another embodiment, the bone fixation plate may be in the form of a periprosthetic ring plate or a periprosthetic hook plate for use in a periprosthetic fracture surrounding, for example, a hip replacement prosthesis. In another embodiment, the bone fixation plate may be in the form of a humerus plate. In either event, the bone fixation plate is designed and configured for fixation across a subsequent fracture in the patient's bone while being designed and configured with one or more features to facilitate avoidance of a previous surgically implanted orthopedic implant.

In one embodiment, the bone fixation plate (e.g., periprosthetic bone plate) may include a head portion, a shaft portion, an upper surface, a lower or bone facing surface, a central longitudinal axis, and an outer periphery surface (e.g., an outer perimeter surface). The shaft portion including a plurality of threaded locking screw openings arranged and configured to receive a plurality of locking screws, respectively. In addition, the shaft portion may include a plurality of variable angled fastener openings arranged and configured to receive a plurality of variable angled screws, respectively. In one embodiment, the plurality of variable angled fastener openings may be positioned along the outer periphery surface of the shaft portion while the plurality of locking screw openings may be centrally located (e.g., positioned closer or substantially adjacent to the central longitudinal axis of the shaft portion).

In one embodiment, the threaded locking screw openings may be larger than the variable angled fastener openings positioned, for example, along the periphery of the shaft portion (e.g., the plurality of threaded locking screw openings include a first diameter and the plurality of variable angled fastener openings include a second diameter, the first diameter being larger than the second diameter). For example, in one embodiment, the threaded locking screw openings may be sized and configured to receive, for example, 4.5 mm locking screws. The variable angled fastener openings may be sized and configured to receive, for example, 3.5 mm bone screws. Alternatively, in some embodiments, the threaded locking screw openings and the variable angled fastener openings may be the same size. For example, in some embodiments, the threaded locking screw openings and the variable angled fastener openings may be sized and configured to receive, for example, 3.5 mm bone screws.

In various embodiments, the shaft portion of the bone fixation plate may include a first region and a second region, the first region being positioned adjacent to the head portion of the bone fixation plate. The plurality of variable angled fastener openings formed in the first region are arranged and configured so that first and second variable angled fastener openings are transversely aligned in a row. That is, the first region may include variable angled fastener openings transversely aligned along the peripheral of the first region of the shaft portion (e.g., the plurality of variable angled fastener openings in the first region are arranged and configured so that first and second variable angled fastener openings are positioned on either side of the central longitudinal axis transversely aligned with each other). The plurality of variable angled fastener openings formed in the second region are non-transversely aligned. That is, the second region may include non-transversely aligned variable angled fastener openings. The plurality of variable angled fastener openings in the second region are arranged and configured so that variable angled fastener openings alternate sides relative to one another (e.g., a single variable angled fastener opening is positioned in a row with each row alternating sides for the variable angled fastener openings as one moves distally on the shaft portion). Thus arranged, the first region of the shaft portion includes a greater number of variable angled fastener openings to provide surgeons with increased options for placing variable angled bone fasteners adjacent to the head portion of the bone fixation plate.

In one embodiment, the bone fixation plate may include a plurality of undercuts formed in the lower surface of the bone plate. In various embodiments, the plurality of undercuts may be aligned or coincident with the plurality of variable angled fastener openings, respectively.

In one embodiment, the bone fixation plate may include a head portion and a shaft portion. The head portion may be contoured for mating with the patient's anatomy such as, for example, the patient's condyle, trochanter, etc. The shaft portion, opposite the head portion, may be arranged and configured to enable contouring of the end portion of the shaft portion. That is, for example, an end portion of the shaft portion, opposite the head portion, may be thinned (e.g., have a reduced cross-sectional area or a tapering cross-sectional area extending from the end portion towards the head portion) to increase the contourablity of the end portion of the bone fixation plate to match the patient's anatomy.

In one embodiment, the end portion may include a plurality of locking screw openings formed therein, the plurality of locking screw openings formed in the end portion including first and second distal locking screw openings, each of the first and second distal locking screw openings including a counterbore formed in the lower surface of the bone plate. In one embodiment, the shaft portion further includes one or more K-wire openings arranged and configured to enable a K-wire to pass therethrough, at least one of the one or more K-wire openings is positioned between the first and second distal locking screw openings. In one embodiment, the end portion of the shaft portion, opposite the head portion, includes a plurality of variable angled fastener openings formed in an array.

In one embodiment, the bone plate is selected from one of a proximal femur plate, a distal femur plate, a periprosthetic ring plate, a periprosthetic hook plate, and a humerus plate.

In one embodiment, the head portion of the bone plate includes a plurality of variable angled screw openings and is devoid of any locking screw openings.

In one embodiment, the head portion of the bone plate includes a plurality of locking screw openings and is devoid of any variable angled fastener openings.

In one embodiment, the head portion includes a plurality of locking screw openings and a plurality of variable angled fastener openings, the plurality of locking screw openings are more centrally located as compared to the plurality of the variable angled fastener openings.

In one embodiment, the plurality of variable angled fastener openings formed in the head portion are arranged and configured in double rows such that the variable angled fastener openings are positioned in transverse rows with first and second variable angled fastener openings positioned in each row.

In one embodiment, the bone fixation plate may be in the form of a ring plate. That is, the bone fixation plate may include a head portion and a shaft portion, the head portion being in the form of a ring arranged and configured for positioning adjacent to a patient's trochanter. In one embodiment, the ring-shaped head portion may be integrally formed with the shaft portion. In one embodiment, the ring-shaped head portion includes a first segment, a second segment spaced from the first segment, and a bridge segment coupling the first and second segments, the ring-shaped head portion including an opening between the first and second segments and the bridge segment. In one embodiment, the bridge segment may include a plurality of variable angle fastener openings centrally positioned thereon.

In addition, and/or alternatively, the ring-shaped head portion may include a plurality of threaded locking screw openings arranged and configured to receive a plurality of locking screws, respectively, and a plurality of variable angled fastener openings arranged and configured to receive a plurality of variable angled fasteners, respectively, the plurality of variable angled fastener openings being dispersed about the plurality of threaded locking screw openings.

In one embodiment, the head portion may include first and second hook members arranged and configured for engaging a patient's trochanter, the first and second hook members being asymmetrical so that the first hook member is different than the second hook member. In one embodiment, the first and second hook members have one of a different size, a different configuration, or a combination thereof.

In one embodiment, a periprosthetic bone plate is disclosed. In one the bone plate includes a head portion, a shaft portion, an upper surface, a lower surface, a central longitudinal axis, and an outer periphery surface. The shaft portion further including a plurality of threaded locking screw openings arranged and configured to receive a plurality of locking screws, respectively and a plurality of variable angled fastener openings arranged and configured to receive a plurality of variable angled screws, respectively; wherein the plurality of threaded locking screw openings include a first diameter and the plurality of variable angled fastener openings include a second diameter, the first diameter being larger than the second diameter.

Embodiments of the present disclosure provide numerous advantages. For example, by incorporating one or more features of the present disclosure, surgeons are provided with increased options for securing a bone fixation plate across a subsequent fracture adjacent to a previous surgically implanted orthopedic device or implant. In addition, by incorporating one or more features of the present disclosure, the bone fixation plates are arranged and configured to allow plating across the major length of the bone. Thus arranged, stress risers that occur at the end of the plate are eliminated, or at least minimized (e.g., as will be appreciated by one of ordinary skill in the art, increased stress risers occur at the end of the plate, which causes increased stress on the bone, which is one contributing factor of periprosthetic fractures. By plating the entire length of the bone such as, for example, the patient's femur, the stress riser is eliminated, or at least greatly minimized).

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which:

FIG. 12 is a top view of an example embodiment of the bone fixation plate in accordance with the present disclosure;

FIG. 13 is a bottom view of the bone fixation plate shown in FIG. 12;

FIG. 15 is a bottom view of an example embodiment of the bone fixation plate shown in FIG. 14; and FIG. 16 is a bottom perspective view of an example embodiment of the bone fixation plate shown in FIG. 14.

Figure 1:
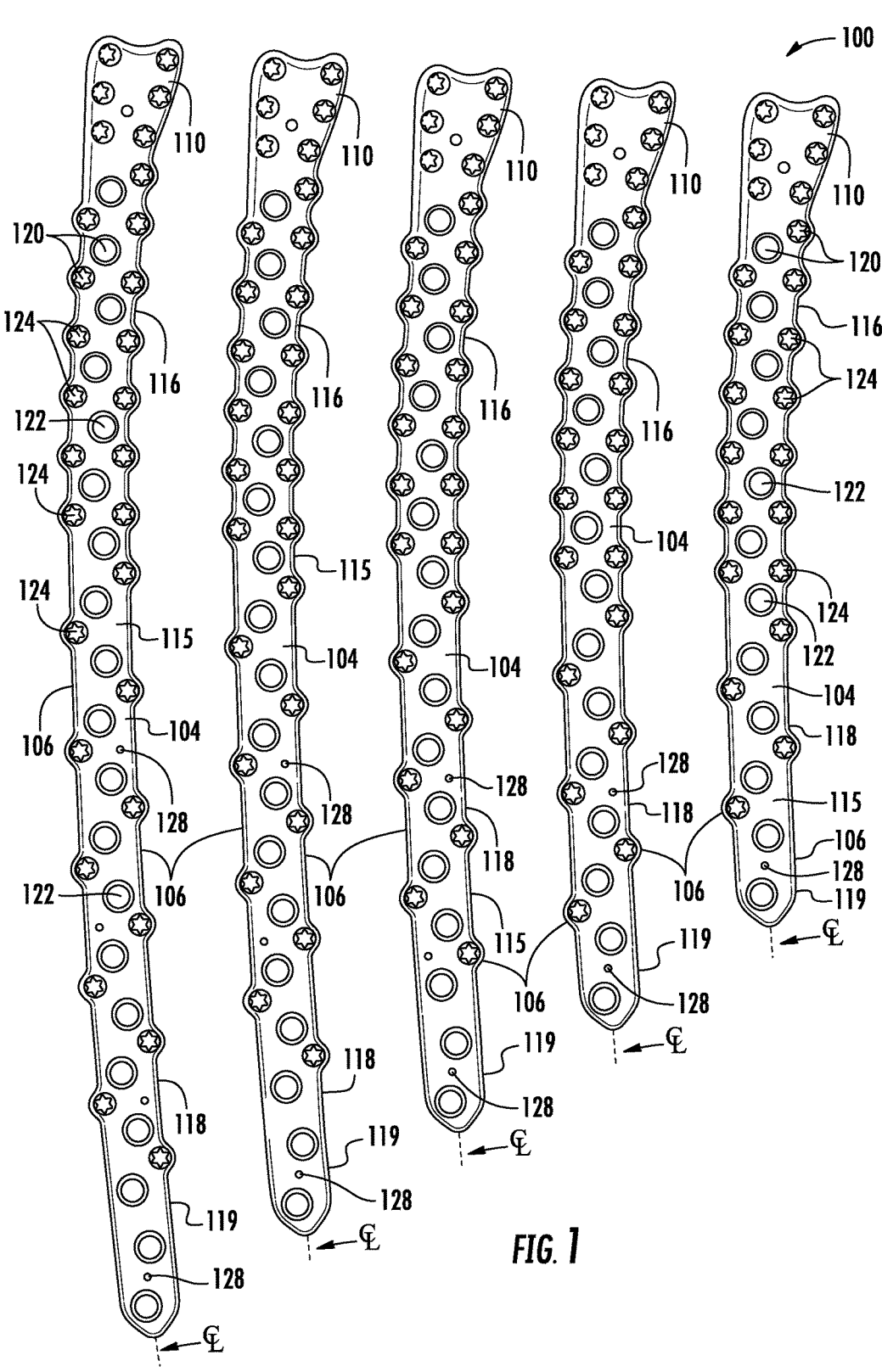
FIG. 1 is a top view of various length bone fixation plates in accordance with the present disclosure.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein.

DETAILED DESCRIPTION

Various features, aspects, or the like of orthopedic bone fixation plates will now be described more fully hereinafter with reference to the accompanying drawings, in which one or more aspects or features of the bone fixation plates will be shown and described. It should be appreciated that the various features, aspects, or the like may be used independently of, or in combination, with each other. It will be appreciated that a bone fixation plate as disclosed herein may be embodied in many different forms and should not be construed as being limited to the embodiments set forth herein. Rather, these embodiments are provided so that this disclosure will convey certain aspects or features of the bone fixation plate to those skilled in the art. In the drawings, like numbers refer to like elements throughout unless otherwise noted.

Disclosed herein are bone fixation plates including one or more aspects or features for enabling increased flexibility for coupling the bone fixation plates to a patient's bone, bone portions, bone fragments, etc. (terms used interchangeably herein without the intent to limit) adjacent to a previous surgically implanted orthopedic implant. That is, as previously mentioned and as will be appreciated by one of ordinary skill in the art, numerous patient's every year undergo surgery where one or more orthopedic devices are implanted. For example, knee replacements, hip replacements, implantation of an IM nail, etc. are commonplace. Occasionally, a bone fracture may occur in the area surrounding the surgically implanted orthopedic implant or device. These fractures are commonly referred to as periprosthetic fractures as they occur adjacent to a previous surgically implanted orthopedic device or implant.

Periprosthetic fractures pose unique fixation challenges. For example, the previous surgically implanted orthopedic device or implant may interfere with the placement and/or securement of the bone fixation plate. For example, in one scenario, an IM nail or stem portion of the previous surgically implanted orthopedic device or implant may interfere with positioning of the bone fixation plate and/or placement of the bone fasteners, screws, or the like (terms used interchangeably herein without the intent to limit) used to secure the bone fixation plate to the patient's bone. In addition, deterioration of the patient's bone surrounding the previous surgically implanted orthopedic device or implant via, for example, osteoporosis, defects in the bone, etc. may further complicate securement and positioning of the bone fixation plate to the patient's bone. As a result, periprosthetic factures and the corresponding techniques for treating periprosthetic fractures are generally more difficult, with limited options.

As such, as will be described herein, the present disclosure discloses a number of bone fixation plates (e.g., periprosthetic bone plates) including one or more features or aspects that may be used in combination or singularly, these features are designed and configured to provide increased flexibility in enabling a surgeon to position and secure a bone fixation plate across a fracture in a patient's bone adjacent to a previous surgically implanted orthopedic device or implant.

As will be described herein, the bone fixation plates may have various shapes and/or configurations. It should be appreciated that the bone fixation plates may be provided in any suitable shape and/or configuration, which, as will be appreciated by one of ordinary skill in the art, may be dependent on the location and type of patient's bone being fixed. For example, a bone fixation plate may include a bone conforming arcuate surface. In addition, the bone fixation plate may be arranged and configured to span, contact, etc. a distal femur, a proximal femur, a distal tibia, a proximal tibia, a proximal humerus, a distal humerus, a fibula, an ulna, a radius, a distal radius, bones of the foot, or bones of the hand, shaft fractures on long bones, etc.

In addition, the bone fixation plate, may include any now known or hereafter developed additional features such as, for example, one or more openings or slots designed to receive, for example, surgical implantation tools, different fasteners (e.g., non-locking fasteners), or the like.

The bone fixation plates may be manufactured from any suitable material now known or hereafter developed, including, for example, metals, polymers, plastics, ceramics, resorbable, non-resorbable, composite materials, etc. Suitable materials may include, for example, titanium, stainless steel, cobalt chrome, polyetheretherketone (PEEK), polyethylene, ultra-high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a patient's body. In some embodiments, the bone fastener may be manufactured from the same material as the bone fixation plate. In other embodiments, the fasteners may be manufactured from a different material as compared to the bone fixation plate.

The fastener can be any type of fastener now known or hereafter developed. For example, the fastener may include any type of external thread including standard or non-standard threads. For example, the external threads can be arranged as a continuous ridge or a non-continuous ridge. The external threads can form a portion of a revolution, one complete revolution, multiple revolutions, a single lead, multiple leads, or any other threads known in the art. Additionally, and/or alternatively, in the case of locking screws, the head portion of the fastener can include any surface that will engage with and seat within a locking screw opening formed in the bone fixation plates. For example, the head portion can include threads. Alternatively, the head portion can include a series of dimples, ridges, bumps, textured areas, or any other surface that can secure the fastener.

The fastener may be any fastener now known or hereafter developed, made out of any appropriate material now known or hereafter developed. The fastener may include a bore for receiving a driver in order to drive the fastener through the bone fixation plate and into the patient's bone. The bore may be any size and shape, for example, it may have a hexagonal configuration to receive a corresponding hexagonal driver, a Phillips screw head, a flat-head, a star configuration, Torx, or any other appropriate configuration that can cooperate with a driver to drive the fastener through the bone fixation plate and into the patient's bone.

The shaft of the fastener may be fully threaded, partially threaded, or a helical blade, and/or may include one or more tacks, deployable talons, expandable elements, or any feature that allows the shaft to engage the patient's bone. It is also possible that shaft be non-threaded so that the fastener takes the form of a peg or a pin. This alternative implementation may be preferred in certain procedures where, for instance, the main goal is to prevent tilting of a bone segment or in procedures where there is no concern of the fastener pulling out from the patient's bone and hence no need for the shaft to be threaded or otherwise configured to engage the patient's bone. The end of the shaft may be a self-tapping or self-drilling tip.

In any event, as will be readily apparent from the remaining disclosure, the focus of the present disclosure is on example embodiments of bone fixation plates including one or more features or aspects arranged and configured to provide increased flexibility for positioning and securing the bone fixation plate adjacent to an area having a previous surgically implanted orthopedic device or implant. Thus, it should be appreciated that the present disclosure should not be limited to any particular configuration of bone fixation plate having any particular configuration unless specifically claimed.

Periprosthetic Proximal Femur Bone Fixation Plate

Referring to FIGS. 1-3B, various embodiments of a bone fixation plate 100 having various lengths for repairing fractures in a patient's bone is disclosed. As will be described herein, the bone fixation plates 100 may be in the form of a proximal femur plate. That is, the bone fixation plate 100 is arranged and configured for positioning adjacent to the proximal femur of a patient. In addition, as will be described herein, the bone fixation plate 100 includes one or more features so that the bone fixation plate 100 facilitates positioning and securement to a patient's proximal femur, which previously was implanted with a surgical orthopedic implant or device such as, for example, an IM nail, a hip prosthetic, etc. As such, the bone fixation plate 100 is arranged and configured for periprosthetic fractures and thus may be referred to as a periprosthetic bone fixation plate or periprosthetic proximal femur bone fixation plate.

As shown, the periprosthetic proximal femur bone fixation plate 100 may include an underside, lower, or bone facing surface 102 (terms used interchangeably herein without the intent to limit) and an upper surface 104. In addition, the periprosthetic proximal femur bone fixation plate 100 includes a head portion 110 and a shaft portion 115. Moreover, the periprosthetic proximal femur bone fixation plate 100 includes a plurality of openings 120 formed therein for receiving a plurality of fasteners (not shown) for coupling the periprosthetic proximal femur bone fixation plate 100 to the patient's bone.

As will be described herein, in accordance with one aspect or feature of the present disclosure, the openings 120 may be in the form of a locking screw (or fastener) opening 122 or a variable angled opening or variable angled fastener (or screw) opening 124 (terms used interchangeably herein without the intent to limit). That is, as will be appreciated by one of ordinary skill in the art, locking screw openings 122 may include a plurality of threads formed on an inner surface thereof for mating with threads formed on an outer surface of a head portion of a bone fastener. Thus arranged, the bone fastener may be said to be locked to the periprosthetic proximal femur bone fixation plate 100 via the locking screw openings 122. That is, as will be appreciated by one of ordinary skill in the art, the bone fastener is threaded through one of the locking screw openings 122 formed in the periprosthetic proximal femur bone fixation plate 100 and into the patient's bone. The bone fastener is secured to the periprosthetic proximal femur bone fixation plate 100 via threads formed on the head portion of the bone fastener that cooperate with the threaded locking screw opening 122 formed in the periprosthetic proximal femur bone fixation plate 100. This secures the periprosthetic proximal femur bone fixation plate 100 with respect to the patient's bone and provides rigid fixation between the periprosthetic proximal femur bone fixation plate 100 and the bone fasteners. That is, because the head portion of the bone fastener interdigitates with the threads formed in the locking screw openings 122 of the periprosthetic proximal femur bone fixation plate 100, the plate 100 and the fasteners form a stable system or construct, and the stability of the fracture can be dependent on or aided by the stiffness of the construct. Locking a bone fastener into the periprosthetic proximal femur bone fixation plate 100 can achieve angular and axial stability and eliminate the possibility for the bone fastener to toggle, slide, or be dislodged, reducing the risk of postoperative loss of reduction.

As previously mentioned, the periprosthetic proximal femur bone fixation plate 100 also includes a plurality of variable angled openings 124 formed therein for receiving a non-locking or variable angled (e.g., polyaxial) bone fastener. In use, the variable angled openings 124 are arranged and configured to enable the bone fastener inserted therein to achieve a greater range of insertion angles as compared to, for example, a conventional locking screw that is threadably coupled to the periprosthetic proximal femur bone fixation plate 100. For example, in one embodiment, the angular position of the bone fastener may be rotated through a range of approximately ±15 degrees, although the range of allowable polyaxial rotation can vary, including greater and less than the fifteen degrees. In use, the variable angled openings 124 may be provided in any suitable manner, configuration, etc. now known or hereafter developed for enabling polyaxial positioning or angling of the bone fastener relative to the periprosthetic proximal femur bone fixation plate 100.

As shown, in one embodiment, the variable angled openings 124 may include fins or projections that extend radially inward from an inner surface of the variable angled openings 124 and into an interior region of the variable angled openings 124, and which are configured to engage or cooperate with the head portion of the bone fastener. In use, the fins engage the head portion of the bone fastener in order to secure the bone fastener at a desired position and at a desired angular orientation within the variable angled opening 124. Additional information on the operation and configuration of the fins can be found in U.S. patent application Ser. No. 15/706,877, with an earliest filing date of Jul. 25, 2005, now U.S. Pat. No. 10,092,337 entitled "Systems and Methods for Using Polyaxial Plates"; U.S. patent application Ser. No. 13/524,506, filed on Jun. 15, 2012, entitled "Variable Angle Locking Implant", and International PCT Patent Application No. PCT/US20/35729, filed on Jun. 2, 2020, entitled "Orthopedic Implant with Improved Variable Angle Locking Mechanism", the entire contents of which are hereby incorporated by reference.

In accordance with one aspect of the present disclosure, the locking screw openings 122 may be arranged and configured to receive larger diameter bone fasteners relative to the variable angled openings 124. That is, for example, the locking screw openings 122 may be arranged and configured to receive 4.5 mm bone fasteners while the variable angled openings 124 may be arranged and configured to receive 3.5 mm bone fasteners, although these dimensions are merely exemplary and other dimensioned bone fasteners are envisioned. By arranging and configuring the periprosthetic proximal femur bone fixation plate 100 to receive larger diameter locking screws, the periprosthetic proximal femur bone fixation plate 100 is better able to be secured to the patient's bone. Meanwhile, by incorporating smaller, variable angled openings 124, the periprosthetic proximal femur bone fixation plate 100 is better able to facilitate positioning of the non-locking screws (e.g., polyaxial variable angled bone screws) around the previous surgically implanted orthopedic device or implant (e.g., smaller non-locking bone fasteners enable a surgeon to better navigate the previous surgically implanted orthopedic device or implant).

In addition, and/or alternatively, in accordance with another aspect or feature of the present disclosure, the locking screw openings 122 may be positioned within the shaft portion 115 of the periprosthetic proximal femur bone fixation plate 100. For example, in one embodiment of the periprosthetic proximal femur bone fixation plate 100, as illustrated, the head portion 110 of the periprosthetic proximal femur bone fixation plate 100 may be completely devoid of any locking screw openings 122, although it is envisioned that the head portion 110 may incorporate one or more locking screw openings 122. Moreover, as shown, the locking screw openings 122 may be more centrally located as compared to the variable angled openings 124 formed in the shaft portion 115. For example, in one embodiment, the shaft portion 115 may include a central longitudinal axis $C_L$, the locking screw openings 122 may be positioned substantially along the central longitudinal axis $C_L$ of the shaft portion 115 of the periprosthetic proximal femur bone fixation plate 100 while the variable angled openings 124 formed in the shaft portion 115, as illustrated, may be positioned along and/or adjacent to an outer periphery or surface 106 of the shaft portion 115 of the periprosthetic proximal femur bone fixation plate 100. That is, the locking screw openings 122 are positioned more interior, closer to the central longitudinal axis $C_L$ of the shaft portion 115 relative to the variable angled openings 124, which are positioned closer to the outer periphery or perimeter surface 106 of the shaft portion 115.

Thus arranged, by positioning the variable angled openings 124 along and/or adjacent to the outer periphery 106 of the shaft portion 115, the periprosthetic proximal femur bone fixation plate 100 is better able to position the variable angled bone fastener to avoid the previous surgically implanted orthopedic device or implant (e.g., the surgeon is better able to position and insert one or more bone fastener through the variable angled openings 124 formed in the periprosthetic proximal femur bone fixation plate 100 while avoiding, for example, the stem portion or IM nail of a previous surgically implanted orthopedic device or implant in the patient's proximal femur).

In addition, and/or alternatively, in accordance with another aspect or feature of the present disclosure, the shaft portion 115 of the periprosthetic proximal femur bone fixation plate 100 may include a first region 116 and a second region 118. As illustrated, the first region 116 may be positioned adjacent to the head portion 110 of the periprosthetic proximal femur bone fixation plate 100. In one or more embodiments, the variable angled openings 124 may be arranged and configured so that they are positioned transversely to one another within the first region 116 of the shaft portion 115. That is, as illustrated, the variable angled openings 124 may be seen as being positioned in transverse rows with two variable angled openings 124 positioned in a row, one along each side or periphery surface 106 of the periprosthetic proximal femur bone fixation plate 100. Thus arranged, the variable angled openings 124 in the first region 116 of the shaft portion 115 may be referred to be positioned in a double row. Meanwhile, as illustrated, the variable angled openings 124 formed in the second region 118 of the shaft portion 115 of the periprosthetic proximal femur bone fixation plate 100 may be arranged so that they alternate relative to each other. That is, as illustrated, the variable angled openings 124 may be seen as being positioned in transverse rows with only a single variable angled opening 124 positioned in a row, with the variable angled openings 124 alternating which side or periphery surface 106 of the periprosthetic proximal femur bone fixation plate 100 it is positioned adjacent too. Thus arranged, as illustrated, the first region 116 of the shaft portion 115 may include more (e.g., double the number of) variable angled openings 124 as compared to the second region 118 of the shaft portion 115 even though the first and second regions 116, 118 of the shaft portion 115 may have the same number of rows of variable angled openings 124, although it is envisioned that the first and second regions 116, 118 may also have different numbers of rows. By positioning the variable angled openings 124 in double rows in the first region 116 of the shaft portion 115, the surgeon is provided with increased options when inserting variable angled bone fasteners into the patient's bone in the expected vicinity of the stem portion or IM nail of the previous surgically implanted orthopedic device or implant. Meanwhile, by providing only a single row of alternating variable angled openings 124 in the second region 118 of the shaft portion 115, the strength of the bone fixation plate 100 is better maintained.

Figure 2:
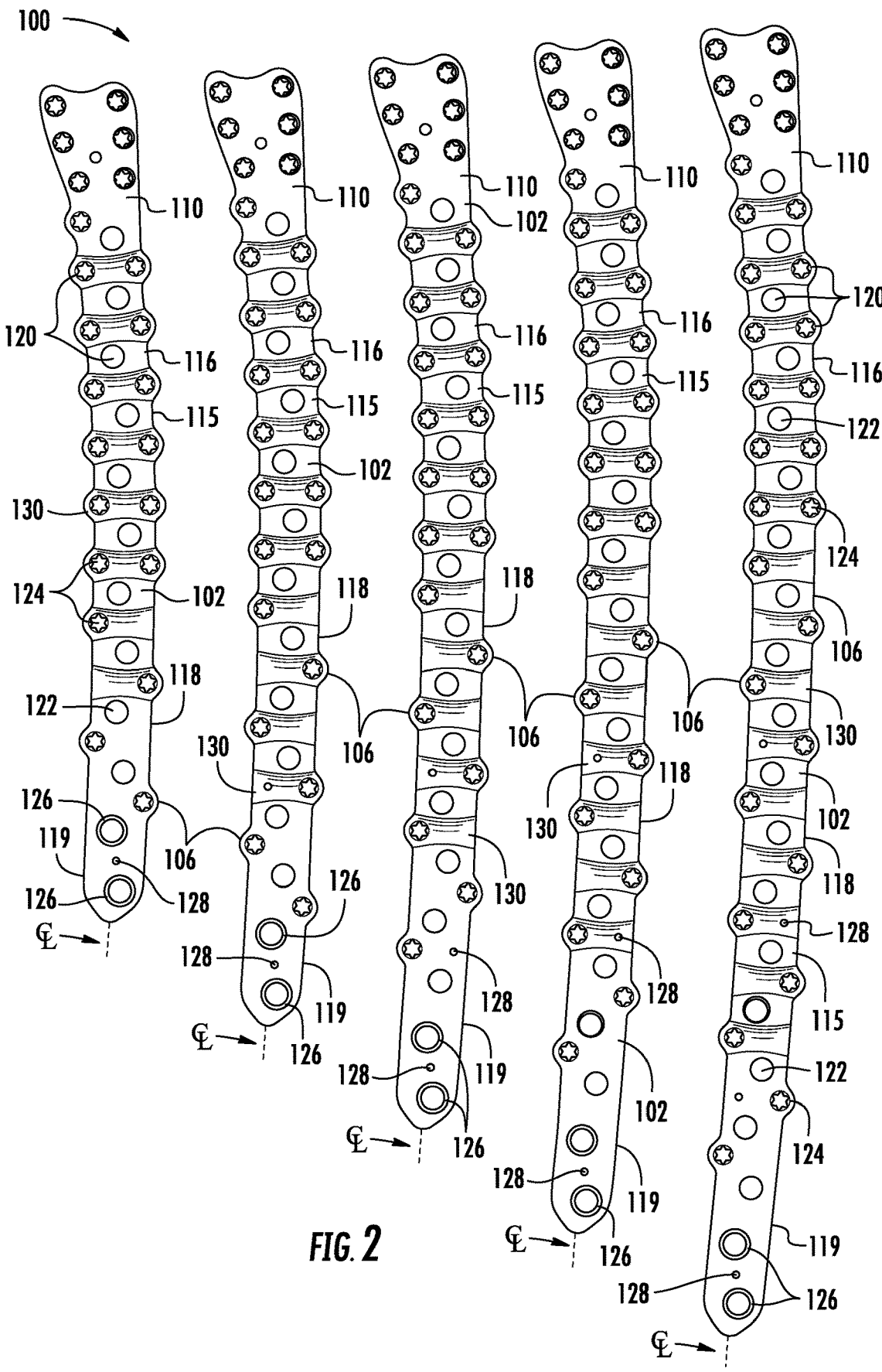
FIG. 2 is a bottom view of the bone fixation plates shown in FIG. 1.
Figures 3A, 3B:
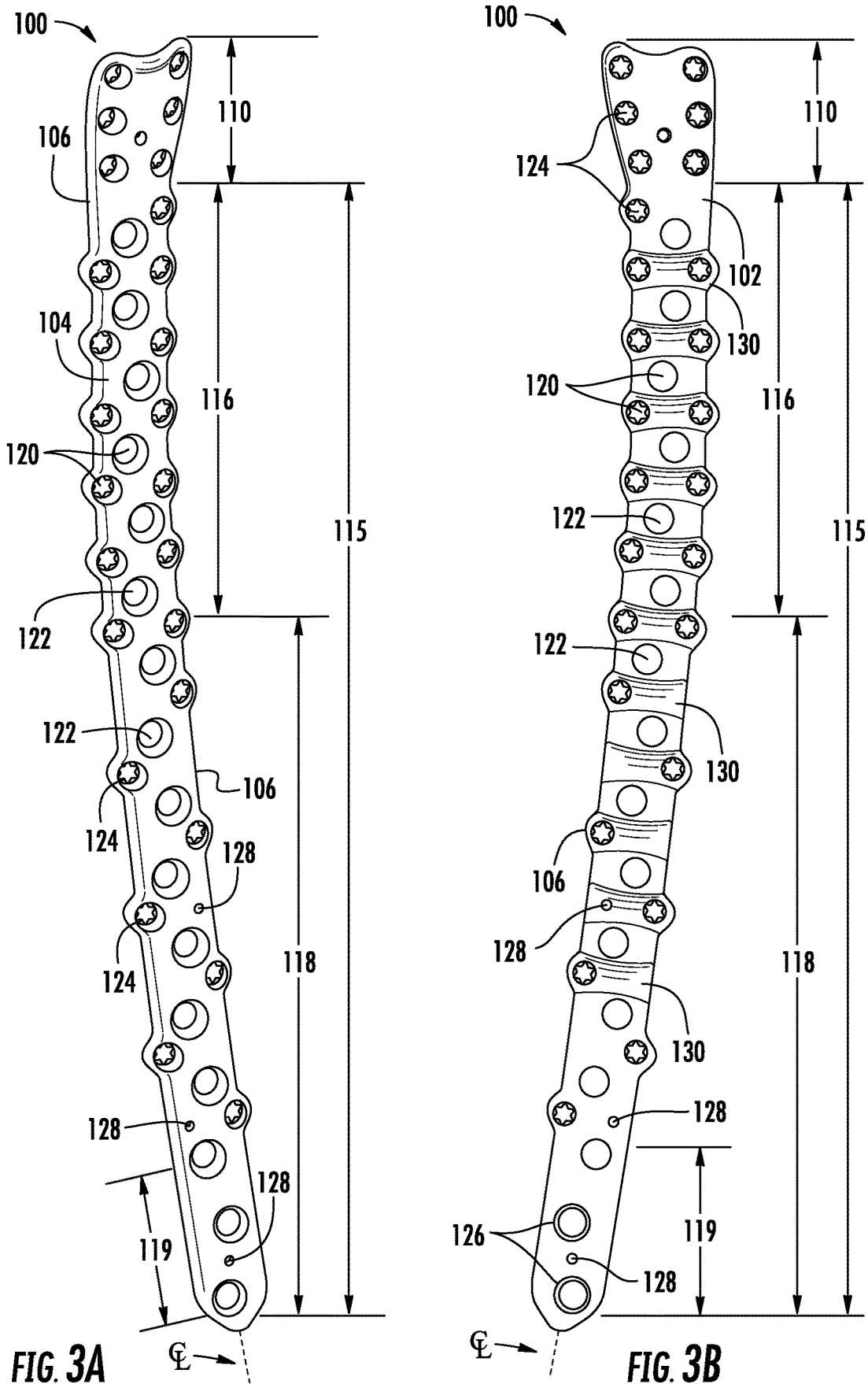
FIG. 3A is a top, perspective view of an example embodiment of the bone fixation plate shown in FIG. 1.
FIG. 3B is a bottom, perspective view of the bone fixation plate shown in FIG. 3A.
Figure 4:
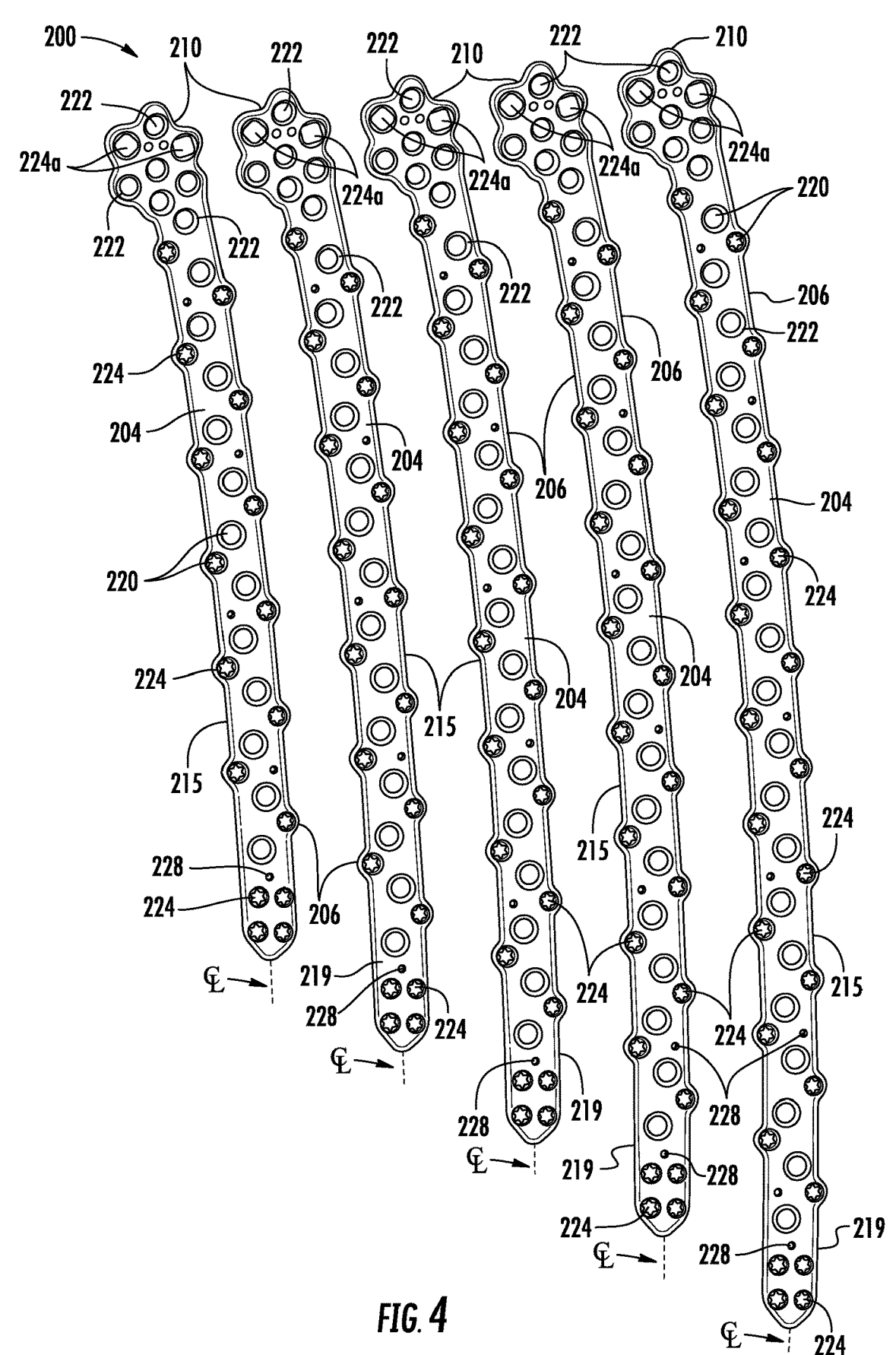
FIG. 4 is a top view of various length bone fixation plates in accordance with the present disclosure.

Referring to FIGS. 2 and 3B, the shaft portion 115 of the periprosthetic proximal femur bone fixation plate 100 may include a plurality of undercuts or grooves 130 formed in the underside or bone facing surface 102. However, in addition, and/or alternatively, in accordance with another aspect or feature of the present disclosure, the plurality of undercuts 130 may be coincidence with or collocated with the variable angled openings 124 formed in the shaft portion 115 of the periprosthetic proximal femur bone fixation plate 100. That is, the variable angled openings 124 formed in the shaft portion 115 may be positioned or reside within the undercuts 130 formed in the bone facing surface 102. In use, the undercuts 130 may be sized and configured to provide clearance for a cable to pass underneath the proximal femur bone fixation plate 100. In one embodiment, the plurality of undercuts 130 are collocated with the variable angled openings 124 formed in the shaft portion 115 of the periprosthetic proximal femur bone fixation plate 100 to provide increased bone plate strength (e.g., the undercuts 130 and the variable angled openings 124 are centered between the central locking screw openings 122, which is the location of the peak stress. If either the undercuts 130 or the variable angled openings 124 were positioned closer to one of the central locking screw openings 122, the overall strength of the plate would be diminished).

In addition, and/or alternatively, in accordance with another aspect or feature of the present disclosure, the distal end portion 119 of the periprosthetic proximal femur bone fixation plate 100 (e.g., end portion opposite the head portion 110) may include thinning That is, the distal end portion 119 may include a reduced or tapering cross-sectional area to facilitate contouring of the distal end portion 119 relative to the patient's anatomy. Generally speaking, as will be appreciated by one of ordinary skill in the art, during use, surgeons often select a bone fixation plate having a length sized and configured to bridge or span the entire area of the fracture. For example, it is not uncommon for a bone fixation plate to extend from and/or to the femur condyle or the patient's trochanter or higher. In use, the head portion of the bone fixation plate may be highly contoured to match the patient's anatomy. However, providing a bone fixation plate with both ends contoured creates numerous issues. For example, generally speaking, providing a bone fixation plate anatomically constrained or contoured at both ends will not fit individual patients as intended. Thus, it is beneficial to anatomically un-constrain one end of the bone plate to enable contouring of the bone plate to provide a better fit for each individual patient. In addition, and/or alternatively, providing a bone fixation plate with both ends contoured creates numerous manufacturing issues. In accordance with one aspect or feature of the present disclosure, the distal end portion 119 (e.g., end portion opposite the head portion 110) may incorporate a reduced cross-sectional area to better enable the surgeon to contour the distal end portion 119 to accommodate the patient's anatomy.

Referring to FIG. 3B, in accordance with another aspect of the present disclosure, the locking screw openings 122 formed in the distal end portion 119 of the shaft portion 115 may include an underside counterbore 126 formed in the underside or bone facing surface 102 thereof. For example, as illustrated, the two distal most locking screw openings 122 formed in the shaft portion 115 of the proximal femur bone fixation plate may include an underside counterbore 126, although it is envisioned that more or less locking screw openings may be counterbored on the underside or bone facing surface 102. In use, by providing a counterbore 126 in the underside or bone facing surface 102 of the locking screw openings 122 formed in the distal end portion 119 of the plate 100, the underside counterbored locking screw openings 126 may be used in combination with an instrument to grab and compress the bone fracture.

The shaft portion 115 of the proximal femur bone fixation plate 100 may also include a plurality of K-wire openings 128 for enabling a K-wire to pass therethrough. As illustrated, in addition, and/or alternatively, in accordance with another aspect or feature of the present disclosure, an initial K-wire opening 128 may be positioned between the distal two most locking screw openings 122. In addition, the shaft portion 115 may include a plurality of additional K-wire openings 128 formed therein. In use, the plurality of K-wire openings 128 allow a surgeon to provisionally hold the bone fixation plate 100 to the patient's bone after they have reduced the fracture.

As generally shown, and as will be appreciated by one of ordinary skill in the art, the number of undercuts, variable angled openings, locking screw openings, etc. will be variable between the various bone fixation plates depending on the length of the plate.

Periprosthetic Distal Femur Bone Fixation Plate

Referring to FIGS. 4-6B, various embodiments of an alternate bone fixation plate 200 having various lengths for repairing fractures in a patient's bone is disclosed. As will be described herein, the bone fixation plates 200 illustrated and described in connection with FIGS. 4-6B may be substantially similar to the periprosthetic proximal femur bone fixation plate 100 described above in connection with FIGS. 1-3B, however the bone fixation plate 200 may be in the form of a distal femur plate. That is, the bone fixation plate 200 is arranged and configured for positioning adjacent to the distal femur of a patient. In addition, as will be described herein, the bone fixation plate 200 includes one or more features so that the bone fixation plate 200 facilitates positioning and securement to a patient's distal femur, which previously received a surgical implanted orthopedic device or implant such as, for example, an IM nail, a knee prosthetic, etc. As such, the bone fixation plate 200 is arranged and configured for periprosthetic fractures and thus may be referred to as a periprosthetic bone fixation plate or periprosthetic distal femur bone fixation plate.

As shown, the periprosthetic distal femur bone fixation plate 200 may include an underside, lower, or bone facing surface 202 and an upper surface 204. In addition, the periprosthetic distal femur bone fixation plate 200 includes a head portion 210 and a shaft portion 215. Moreover, the periprosthetic distal femur bone fixation plate 200 includes a plurality of openings 220 formed therein for receiving a plurality of fasteners (not shown) for coupling the periprosthetic distal femur bone fixation plate 200 to the patient's bone.

As previously described in connection with the proximal femur bone fixation plate 100, the periprosthetic distal femur bone fixation plate 200 may include a plurality of locking screw openings 222 and a plurality of variable angled openings 224. Similar to the locking screw openings 222 and variable angled openings 224 described in connection with the proximal femur bone fixation plate 100, and in accordance with one aspect of the present disclosure, the locking screw openings 222 formed in the periprosthetic distal femur bone fixation plate 200 may be arranged and configured to receive larger diameter bone fasteners relative to the variable angled openings 224 formed in the periprosthetic distal femur bone fixation plate 200. That is, for example, the locking screw openings 222 may be arranged and configured to receive 4.5 mm bone fasteners while the variable angled openings 224 may be arranged and configured to receive 3.5 mm bone fasteners, although these dimensions are merely exemplary and other dimensioned bone fasteners are envisioned. By arranging and configuring the periprosthetic distal femur bone fixation plate 200 to receive larger diameter locking screws, the periprosthetic distal femur bone fixation plate 200 is better able to be secured to the patient's bone. Meanwhile, by incorporating smaller, variable angled openings 224, the periprosthetic distal femur bone fixation plate 200 is better able to facilitate positioning of the non-locking screws (e.g., polyaxial variable angled bone screws) around the previous surgically implanted orthopedic device or implant.

In addition, and/or alternatively, in accordance with another aspect or feature of the present disclosure and as previously described, the locking screw openings 222 may be positioned within the shaft portion 215 of the periprosthetic distal femur bone fixation plate 200. As shown, the locking screw openings 222 may be more centrally located as compared to the variable angled openings 224 formed in the shaft portion 215. As illustrated, the variable angled openings 224 may be positioned along and/or adjacent to an outer periphery or surface 206 of the shaft portion 215 of the periprosthetic distal femur bone fixation plate 200. For example, in one embodiment, the shaft portion 215 may include a central longitudinal axis $C_L$, the locking screw openings 222 may be positioned substantially along the central longitudinal axis $C_L$ of the shaft portion 215 of the periprosthetic proximal femur bone fixation plate 200 while the variable angled openings 224 may be positioned along and/or adjacent to an outer periphery or surface 206 of the shaft portion 215 of the periprosthetic distal femur bone fixation plate 200. That is, the locking screw openings 222 are positioned more interior, closer to the central longitudinal axis $C_L$ of the shaft portion 215 relative to the variable angled openings 224, which are positioned closer to the outer periphery or perimeter surface 206 of the shaft portion 215.

Thus arranged, by positioning the variable angled openings 224 along and/or adjacent to the outer periphery 206 of the shaft portion 215, the periprosthetic distal femur bone fixation plate 200 is better able to position the variable angled bone fastener to avoid the previous surgically implanted orthopedic device or implant (e.g., the surgeon is better able to position and insert one or more bone fastener through the variable angled openings 224 formed in the periprosthetic distal femur bone fixation plate 200 while avoiding, for example, a stem portion of a knee prosthetic or IM nail of a previous surgically implanted orthopedic device or implant in the patient's distal femur).

As shown, in one embodiment, in connection with the periprosthetic distal femur bone fixation plate 200, the head portion 210 of the periprosthetic distal femur bone fixation plate 200 may include a plurality of locking screw openings 222. In one embodiment, the head portion 210 may also include one or more larger-diameter variable angled holes 224a (e.g., arranged and configured to receive 4.5 mm bone fasteners). Alternatively, the head portion 210 of the periprosthetic distal femur bone fixation plate 200 may be completely devoid of any variable angled openings 224 (e.g., the head portion 215 of the periprosthetic distal femur bone fixation plate 200 may include exclusively locking screw openings 222). Alternatively, it is envisioned that the head portion 210 of the periprosthetic distal femur bone fixation plate 200 may include one or more smaller diameter variable angled openings 224 (arranged and configured to receive 3.5 mm bone fasteners).

In addition, as shown, in connection with the periprosthetic distal femur bone fixation plate 200, the shaft portion 215 of the periprosthetic distal femur bone fixation plate 200 may exclusively incorporate single rows of alternately variable angled openings 224 (e.g., shaft portion 215 may be devoid of any double rows of variable angled openings 224 as previously described). However, while not shown, it is envisioned that the shaft portion 215 of the periprosthetic distal femur bone fixation plate 100 may include first and second regions similar to the periprosthetic proximal femur bone fixation plate 100 wherein, in the first region, the variable angled openings are transversely positioned/aligned with each other and in the second region, the variable angled openings may be alternately positioned so that the first region of the shaft portion includes more variable angled openings as compared to the second region thereby providing the surgeon with increased options when inserting bone fasteners into the patient's bone in the expected vicinity of the previous surgically implanted orthopedic device or implant.

Figure 5:
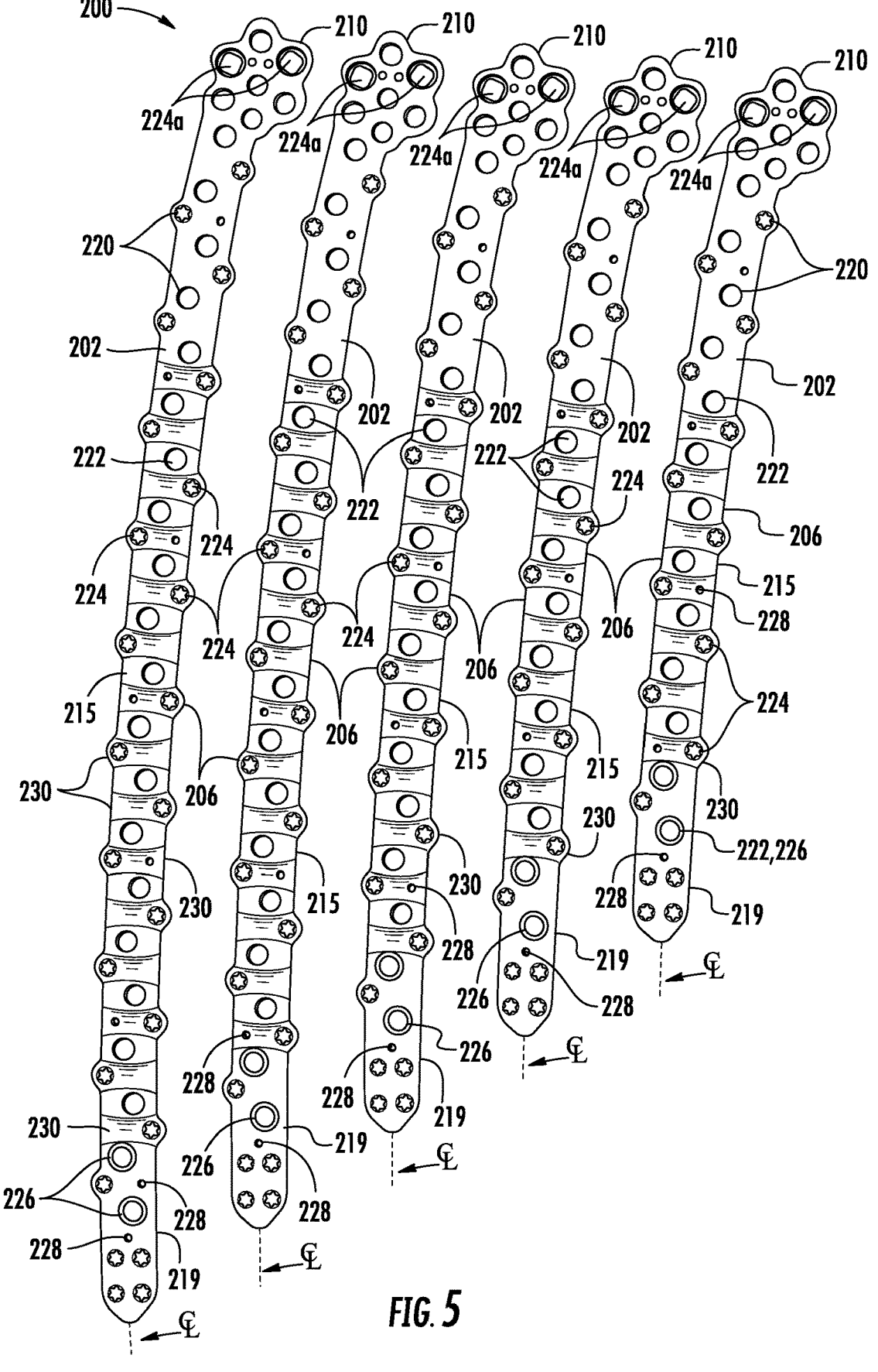
FIG. 5 is a bottom view of the bone fixation plates shown in FIG. 4.
Figure 6:
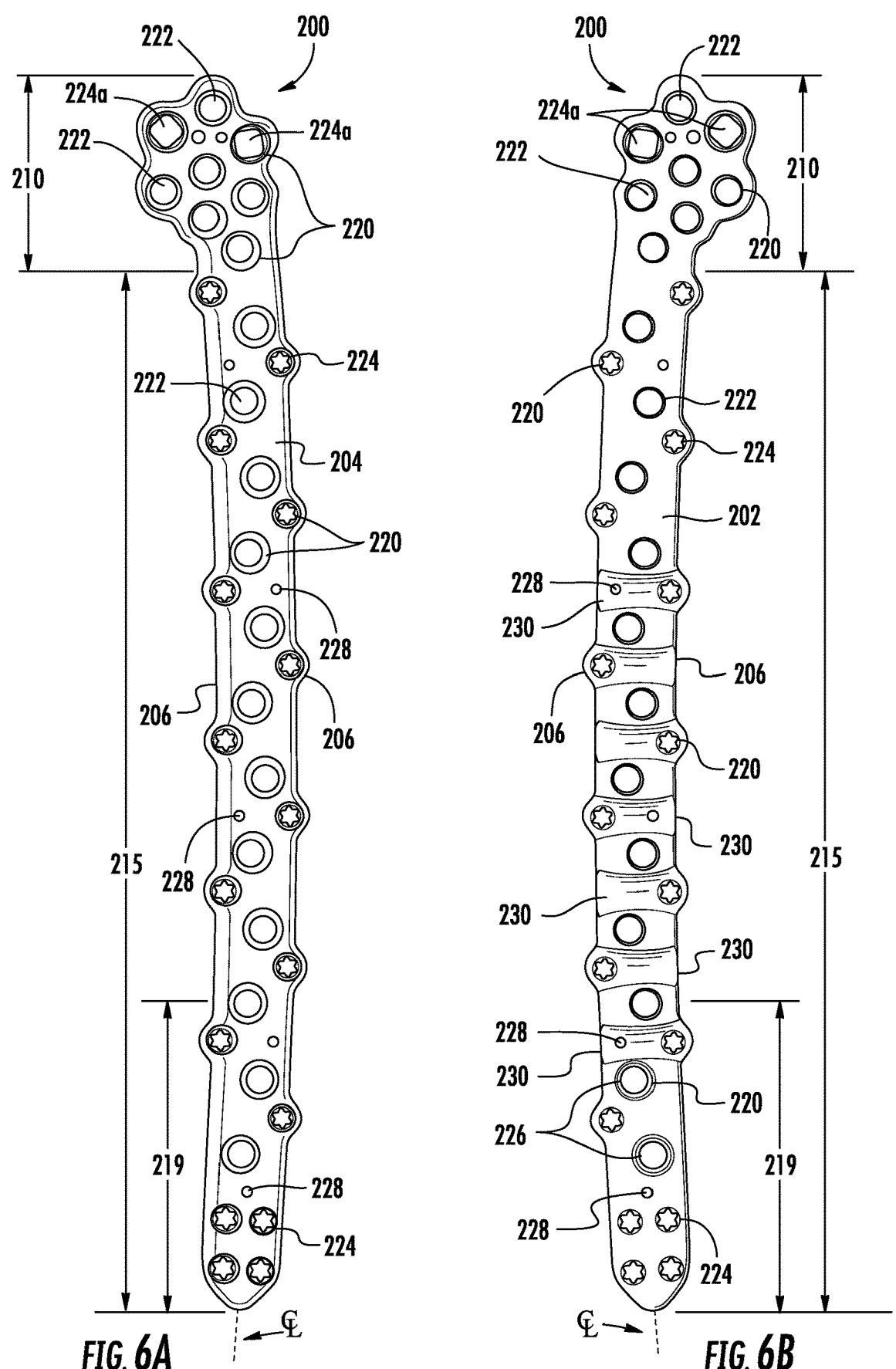
FIG. 6A is a top view of an example embodiment of the bone fixation plate shown in FIG. 4.
FIG. 6B is a bottom view of the bone fixation plate shown in FIG. 6A.

Referring to FIGS. 5 and 6B, the shaft portion 215 of the periprosthetic distal femur bone fixation plate 200 may include a plurality of undercuts or grooves 230 formed in the underside or bone facing surface 202. However, in addition, and/or alternatively, in accordance with another aspect or feature of the present disclosure, the plurality of undercuts 230 may be coincidence with or collocated with the variable angled openings 224 formed in the shaft portion 215 of the periprosthetic distal femur bone fixation plate 200. That is, the variable angled openings 224 formed in the shaft portion 215 may be positioned or reside within the undercuts 230 formed in the bone facing surface 202. In use, the undercuts 230 may be sized and configured to provide clearance for a cable to pass underneath the distal femur bone fixation plate 100. As previously mentioned, in one embodiment, the plurality of undercuts 230 are collocated with the variable angled openings 224 formed in the shaft portion 215 of the periprosthetic distal femur bone fixation plate 200 to provide increased bone plate strength (e.g., the undercuts 230 and the variable angled openings 224 are centered between the central locking screw openings 222, which is the location of the peak stress. If either the undercuts 230 or the variable angled openings 224 were positioned closer to one of the central locking screw openings 222, the overall strength of the plate would be diminished).

In addition, and/or alternatively, in accordance with another aspect or feature of the present disclosure and as previously described in connection with the periprosthetic proximal femur bone fixation plate 100, an end portion 219 of the periprosthetic distal femur bone fixation plate 200 (e.g., a proximal end portion 219 opposite the head portion 210) of the periprosthetic distal femur bone fixation plate 200 may include thinning That is, the end portion 219 of the shaft portion 215 may include a reduced or tapering cross-sectional area to facilitate contouring of the end portion relative to the patient's anatomy. That is, as previous mentioned, in accordance with one aspect or feature of the present disclosure, the end portion 219 of the shaft portion 215 (e.g., end portion 219 opposite the head portion 210) may incorporate a reduced cross-sectional area to better enable the surgeon to contour the end portion 219 to accommodate the patient's anatomy. For example, as previously mentioned, providing a bone fixation plate with both ends contoured creates numerous issues. For example, generally speaking, providing a bone fixation plate anatomically constrained or contoured at both ends will not fit individual patients as intended. Thus, it is beneficial to anatomically un-constrain one end of the bone plate to enable contouring of the bone plate to provide a better fit for each individual patient. In accordance with one aspect or feature of the present disclosure, the end portion 219 (e.g., end portion opposite the head portion 210) may incorporate a reduced cross-sectional area to better enable the surgeon to contour the end portion 219 to accommodate the patient's anatomy.

In addition, as illustrated in FIG. 6B, the end portion 219 of the periprosthetic distal femur bone fixation plate 200 may include a plurality of variable angled openings 224 (e.g., the end portion 219 may include exclusively, or a majority of, variable angled openings 224). As shown, for example, the variable angled openings 224 formed in the end portion 219 may be arranged in an array such as, for example, a 2×2 array, although this is merely exemplary and other arrays and/or configurations are envisioned. By providing an array of variable angled openings 224 in the end portion 219, a surgeon is provided with increased options for positioning variable angled bone fasteners into the patient's bone (e.g., in use, the end portion 219 is designed to reach the proximal femur at which point the bone is no longer diaphyseal, the variable angle holes allow screws to reach more desirable bone and lengths. For example, screws may target the lesser trochanter, femoral head, or some other desired region in the proximal femur).

In addition, referring to FIG. 6B, in accordance with another aspect of the present disclosure and as previously described above in connection with the periprosthetic proximal femur bone fixation plate 100, the locking screw openings 222 formed in the end portion 219 (e.g., opposite the head portion 210) may include an underside counterbore 226 formed in the underside or bone facing surface 202 thereof. For example, as illustrated, the two proximal most locking screw openings 222 formed in the shaft portion 215 of the periprosthetic distal femur bone fixation plate 210 may include an underside counterbore 226, although it is envisioned that more or less locking screw openings 222 may be counterbored on the underside or bone facing surface 202. In use, by providing a counterbore 226 in the underside or bone facing surface 202 of the locking screw openings 222 formed in the end portion 219 of the plate 200, the underside counterbored locking screw openings may be used in combination with an instrument to grab and compress the bone fracture.

As previously mentioned, the shaft portion 215 of the periprosthetic distal femur bone fixation plate 200 may also include a plurality of K-wire openings 228 for enabling a K-wire to pass therethrough. As illustrated, in addition, and/or alternatively, in accordance with another aspect or feature of the present disclosure, an initial K-wire opening 228 may be positioned between the array of variable angled openings 224 and the proximal most locking screw opening 222. In addition, the shaft portion 215 may include a plurality of additional K-wire openings 228 formed therein. In use, the plurality of K-wire openings 228 allow a surgeon to provisionally hold the bone fixation plate 200 to the patient's bone after they have reduced the fracture.

As generally shown, and as will be appreciated by one of ordinary skill in the art, the number of undercuts, variable angled openings, locking screw openings, etc. will be variable between the various bone fixation plates depending on the length of the plate.

Periprosthetic Humerus or Utility Bone Fixation Plate

Figure 7:
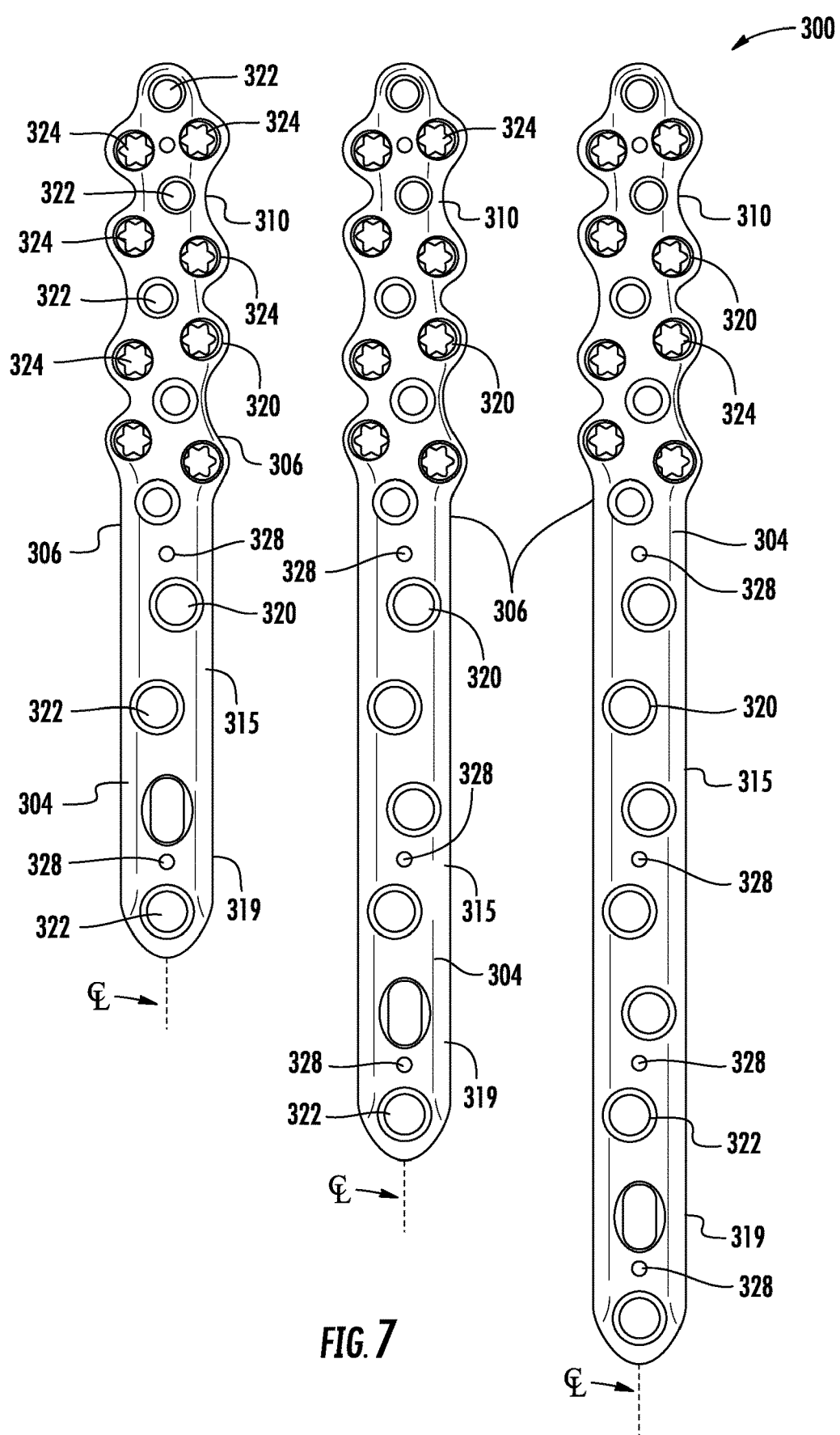
FIG. 7 is a top view of various length bone fixation plates in accordance with the present disclosure.
Figure 8:
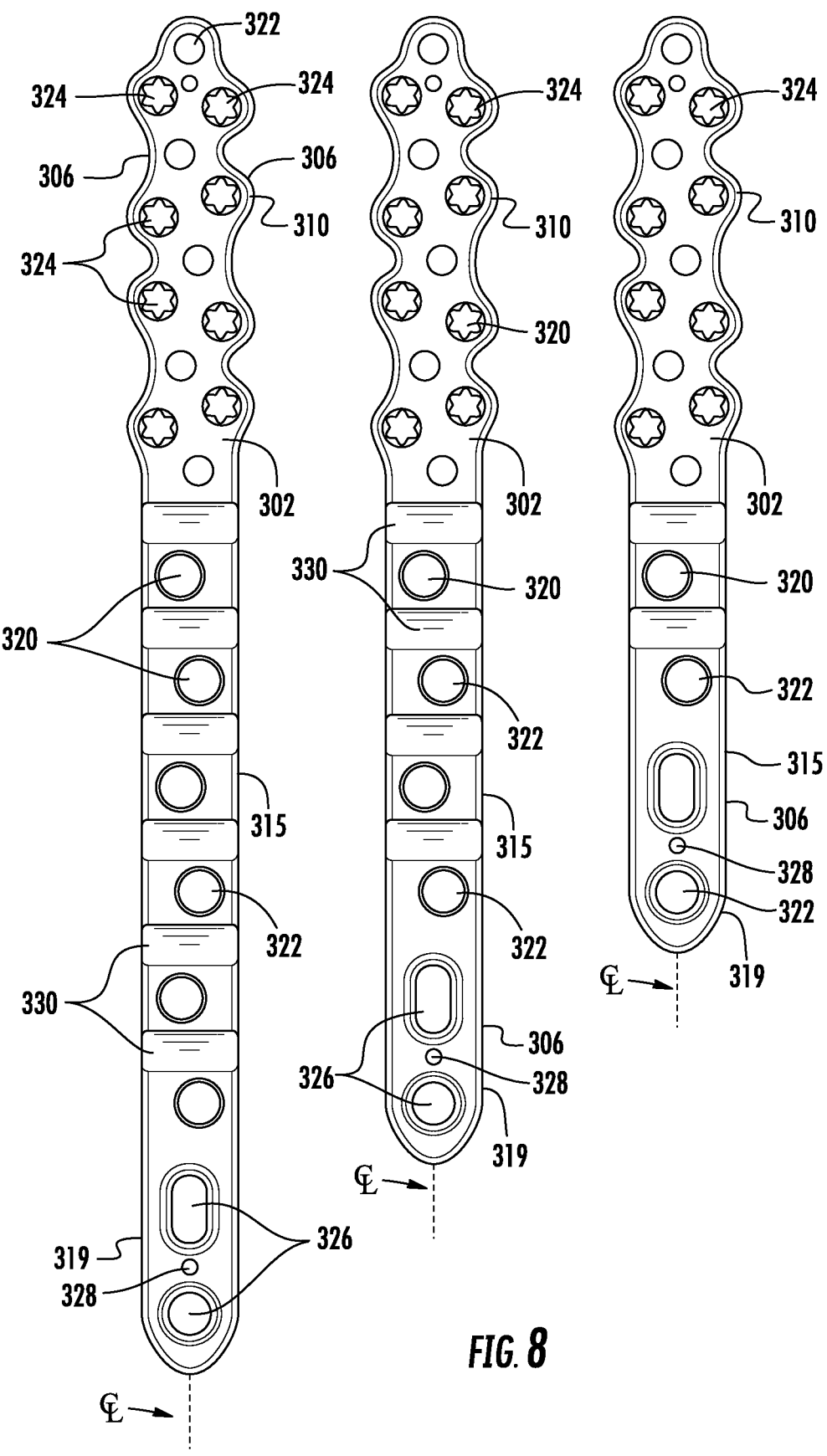
FIG. 8 is a bottom view of the bone fixation plates shown in FIG. 7.
Figure 9:
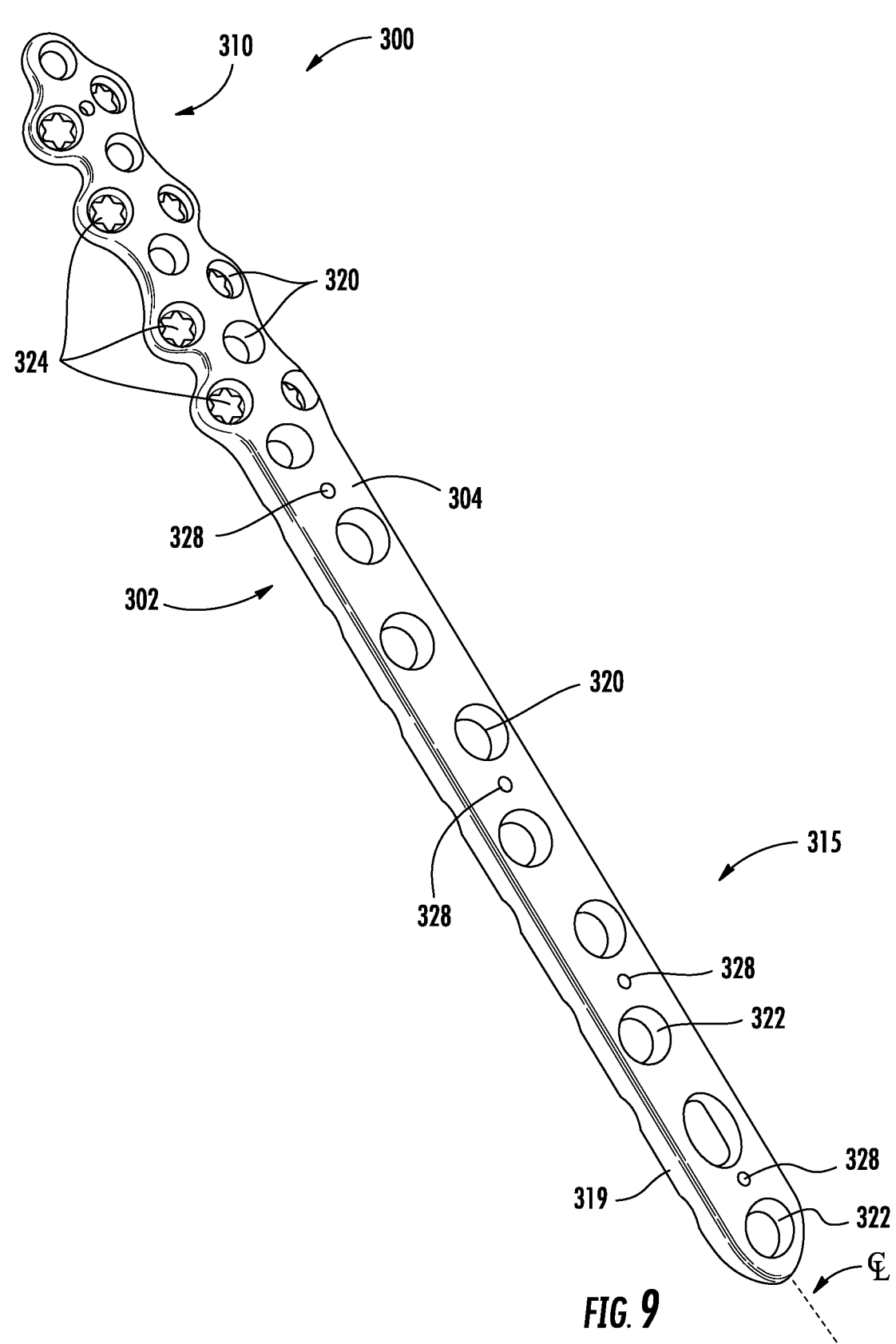
FIG. 9 is a top, perspective view of an example embodiment of the bone fixation plate shown in FIG. 7.

Referring to FIGS. 7-9, various embodiments of an alternate bone fixation plate 300 having various lengths for repairing fractures in a patient's bone is disclosed. As will be described herein, the bone fixation plates 300 illustrated and described in connection with FIGS. 7-9 may include some or all of the features or aspects described above in connection with the periprosthetic proximal and distal femur bone fixation plates 100, 200. However, the bone fixation plate 300 may be in the form of a humerus or utility plate. That is, the bone fixation plate 300 is arranged and configured for positioning against a long bone of a patient such as, for example, the humerus of a patient. In addition, generally speaking, in a periprosthetic long bone fracture, the amount of remaining bone for receiving bone fixation screws may be minimal. Typically, the remaining bone portion will likely only be in alignment with the shaft portion of the plate. Thus, generally speaking, the utility plate may be less contoured as compared to various other bone fixation plates described herein. One advantage of this, is that the utility plate may be arranged and configured to work with many long bones such as, for example, the patient's humerus, thus the utility plate may act or be referred to as a periprosthetic humerus plate.

Moreover, as will be described herein, the bone fixation plate 300 includes one or more features so that the bone fixation plate 300 facilitates positioning and securement to a patient's long bone (such as, for example, humerus bone), which previously received a surgically implanted orthopedic implant or device such as, for example, an IM nail, etc. As such, the bone fixation plate 300 is arranged and configured for periprosthetic fractures and thus may be referred to as a periprosthetic bone fixation plate, a periprosthetic utility bone fixation plate, or a periprosthetic humerus bone fixation plate.

As shown, the periprosthetic utility bone fixation plate 300 may include an underside, lower, or bone facing surface 302 and an upper surface 304. In addition, the periprosthetic utility bone fixation plate 300 includes a head portion 310 and a shaft portion 315. Moreover, the periprosthetic utility bone fixation plate 300 includes a plurality of openings 320 formed therein for receiving a plurality of fasteners (not shown) for coupling the periprosthetic utility bone fixation plate 300 to the patient's bone.

As previously described in connection with the proximal femur bone fixation plate 100, the periprosthetic utility bone fixation plate 300 may include a plurality of locking screw openings 322 and a plurality of variable angled openings 324. Similar to the locking screw openings 122 and variable angled openings 124 described in connection with the proximal femur bone fixation plate 100, and in accordance with one aspect of the present disclosure, the locking screw openings 322 formed in the periprosthetic utility bone fixation plate 300 may be arranged and configured to receive larger diameter bone fasteners relative to the variable angled openings 324 formed in the periprosthetic utility bone fixation plate 300. That is, for example, the locking screw openings 322 may be arranged and configured to receive 4.5 mm bone fasteners while the variable angled openings 324 may be arranged and configured to receive 3.5 mm bone fasteners, although these dimensions are merely exemplary and other dimensioned bone fasteners are envisioned. For example, in some embodiments, the locking screw openings 322 may be arranged and configured to receive other sized bone fasteners such as, for example, 3.5 mm bone fasteners.

By arranging and configuring the periprosthetic utility bone fixation plate 300 to receive larger diameter locking screws, the periprosthetic utility bone fixation plate 300 is better able to secure to the patient's bone. Meanwhile, by incorporating smaller, variable angled openings 324, the periprosthetic utility bone fixation plate 300 is better able to facilitate positioning of the non-locking screws (e.g., polyaxial variable angled bone screws) around the previous surgically implanted orthopedic device or implant.

In connection with the periprosthetic utility bone fixation plate 300, the locking screw openings 322 may be positioned within the shaft portion 315 of the periprosthetic utility bone fixation plate 300. As shown, the locking screw openings 322 may be centrally located. For example, in one embodiment, the shaft portion 315 may include a central longitudinal axis $C_L$, the locking screw openings 322 may be substantially centrally located along the central longitudinal axis $C_L$ of the periprosthetic utility bone fixation plate 300. Moreover, as illustrated, the shaft portion 315 of the periprosthetic utility bone fixation plate 300 may be completely devoid of any variable angled openings 324, although it is envisioned that the shaft portion 315 may include one or more variable angled openings 324.

In addition, and/or alternatively, as illustrated, the head portion 310 of the periprosthetic utility bone fixation plate 300 may include a plurality of locking screw openings 322 and a plurality of variable angled openings 324. As shown, the locking screw openings 322 may be centrally located. For example, in one embodiment, the locking screw openings 322 may be substantially centrally located along the central longitudinal axis $C_L$ of the head portion 310 of the periprosthetic utility bone fixation plate 300 as compared to the variable angled openings 324, which as illustrated, may be positioned along and/or adjacent to an outer periphery or surface 306 of the periprosthetic utility bone fixation plate 300. That is, the locking screw openings 322 are positioned more interior, closer to the central longitudinal axis $C_L$ of the head portion 310 relative to the variable angled openings 324, which are positioned closer to the outer periphery or perimeter surface 306 of the head portion 310. Thus arranged, by positioning the variable angled openings 324 along and/or adjacent to the outer periphery or surface 306 of the head portion 310, the periprosthetic utility bone fixation plate 300 is better able to position the variable angled bone fasteners to avoid the previous surgically implanted orthopedic device or implant (e.g., the surgeon is better able to position and insert one or more bone fastener through the variable angled openings 324 formed in the periprosthetic utility bone fixation plate 300 while avoiding, for example, an IM nail or other previous surgically implanted orthopedic device or implant in the patient's bone).

In addition, and/or alternatively, as illustrated, the variable angled openings 324 formed in the head portion 310 of the periprosthetic utility bone fixation plate 300 may be arranged and configured in double rows as previously described (e.g., the variable angled openings 324 may be seen as being positioned in transverse rows with two variable angled openings 324 positioned in each row, such as, for example, one on each side surface of the central longitudinal axis $C_L$).

Referring to FIG. 8, the shaft portion 315 of the periprosthetic utility bone fixation plate 300 may include a plurality of undercuts or grooves 330 formed in the underside or bone facing surface 302. The undercuts 330 may be positioned on either side of the locking screw openings 322 (e.g., an undercut or groove 330 may be positioned in-between adjacent locking screw openings 322). In use, the undercuts 330 may be sized and configured to provide clearance for a cable to pass underneath the periprosthetic utility bone fixation plate.

In addition, referring to FIG. 8, in accordance with another aspect of the present disclosure and as previously described above in connection with the periprosthetic proximal and distal femur bone fixation plates 100, 200, the locking screw openings 322 formed in the end portion 319 of the periprosthetic utility bone fixation plate 300 (e.g., end portion opposite the head portion 310) may include an underside counterbore 326 formed in the underside or bone facing surface 302 thereof. For example, as illustrated, the two distal most locking screw openings 322 formed in the shaft portion 315 of the periprosthetic utility bone fixation plate 300 may include an underside counterbore 326, although it is envisioned that more or less locking screw openings may be counterbored on the underside or bone facing surface. In use, by providing a counterbore 326 in the underside or bone facing surface 302 of the locking screw openings 322 formed in the end portion 319 of the plate 300, the underside counterbored locking screw openings may be used in combination with an instrument to grab and compress the bone fracture.

The shaft portion 315 of the periprosthetic utility bone fixation plate 300 may also include a plurality of K-wire openings 328 for enabling a K-wire to pass therethrough. As illustrated, in addition, and/or alternatively, in accordance with another aspect or feature of the present disclosure, an initial K-wire opening 328 may be positioned between the distal two most locking screw openings 322. In addition, while not shown, it is envisioned that the shaft portion 315 may include a plurality of additional K-wire openings 328 formed therein.

As generally shown, and as will be appreciated by one of ordinary skill in the art, the number of undercuts, variable angled openings, locking screw openings, etc. will be variable between the various bone fixation plates depending on the length of the plate.

While not shown, it is envisioned that the shaft portion of the periprosthetic utility bone fixation plate 300 may include first and second regions similar to the periprosthetic proximal femur bone fixation plate 100 wherein, in the first region, the variable angled openings are transversely positioned/aligned with each other and in the second region, the variable angled openings may be alternately positioned so that the first region of the shaft portion may include more variable angled openings as compared to the second region of the shaft portion thereby providing surgeons with increased options when inserting bone fasteners into the patient's bone in the expected vicinity of the previous surgically implanted orthopedic device or implant. In addition, and/or alternatively, it is envisioned that the shaft portion of the periprosthetic utility bone fixation plate may include a plurality of variable angled openings and a plurality of undercuts that may be coincidence with or collocated with the variable angled openings.

In addition, and/or alternatively, it is envisioned that the end portions of the periprosthetic utility bone fixation plate may include thinning (e.g., a reduced or tapering cross-sectional area to facilitate contouring of the end portion relative to the patient's anatomy). For example, as previously mentioned, providing a periprosthetic utility bone fixation plate with both ends contoured creates numerous issues. For example, generally speaking, providing a bone fixation plate anatomically constrained or countered at both ends will not fit individual patients as intended. Thus, it is beneficial to anatomically un-constrain one or both ends of the periprosthetic utility bone fixation plate to enable contouring of the bone plate to provide a better fit for each individual patient. In accordance with one aspect or feature of the present disclosure, one or both end portions of the periprosthetic utility bone fixation plate may incorporate a reduced cross-sectional area to better enable the surgeon to contour the end portions to accommodate the patient's anatomy.

Periprosthetic Ring Bone Fixation Plate

Referring to FIGS. 10-13, various embodiments of an alternate bone fixation plate 400 having various lengths for repairing fractures in a patient's bone is disclosed. As will be described herein, the bone fixation plates 400 illustrated and described in connection with FIGS. 10-13 may be substantially similar to the periprosthetic proximal femur bone fixation plate 100 described above in connection with FIGS. 1-3B, however the bone fixation plate 400 may be in the form of a ring plate. That is, the bone fixation plate 400 includes a head portion 410 that is arranged and configured in the configuration of a ring for positioning adjacent to the trochanter of a patient. In addition, as will be described herein, the bone fixation plate 400 includes one or more features so that the bone fixation plate 400 facilitates positioning and securement to a patient's bone such as, for example, a patient's femur, which previously received a surgically implanted orthopedic implant or device such as, for example, an IM nail, a hip prosthetic, etc. As such, the bone fixation plate 400 is arranged and configured for periprosthetic fractures and thus may be referred to as a periprosthetic bone fixation plate or periprosthetic ring bone fixation plate.

As shown, the periprosthetic ring bone fixation plate 400 may include an underside, lower, or bone facing surface 402 and an upper surface 404. In addition, the periprosthetic ring bone fixation plate 400 includes a head portion 410 and a shaft portion 415. Moreover, the periprosthetic ring bone fixation plate 400 includes a plurality of openings 420 formed therein for receiving a plurality of fasteners (not shown) for coupling the periprosthetic ring bone fixation plate 400 to the patient's bone.

As shown, the head portion 410 of the periprosthetic ring bone fixation plate 400 may be arranged and configured as a ring for contacting a patient's trochanter. That is, as shown, the head portion 410 may include a first leg or segment 412, a second leg or segment 413 spaced from the first leg or segment 412, and a bridge segment 414 for coupling the ends of the first and second legs 412, 413. Thus arranged, the head portion 410 includes an opening 411 between the first and second legs 412, 413 and the bridge segment 414. However, in contrast to known ring plates, the periprosthetic ring bone fixation plate 400 may be integrally formed. That is, the ring shaped, head portion 410 of the periprosthetic ring bone fixation plate 400 may be integrally formed with the shaft portion 415 of the periprosthetic ring bone fixation plate 400. By providing an integrally formed periprosthetic ring bone fixation plate 400, the periprosthetic ring bone fixation plate 400 is less likely to break when subjected to fatigue loading. In addition, there are fewer required surgical steps as there is no required assembling of the ring to the plate. Moreover, the periprosthetic ring bone fixation plate 400 facilitates incorporation of more, smaller openings 420 for receiving a plurality of fasteners as compared to fewer, larger openings (e.g., with the hip stem in the way, the smaller 3.5 mm openings enable a surgeon to better avoid the hip stem while maintaining the stability to resist the deforming forces from attached muscles).

In addition, and/or alternatively, in accordance with another aspect or feature of the present disclosure, the head portion 410 of the periprosthetic ring bone fixation plate 400 may include a plurality of locking screw openings 422 and a plurality of variable angled openings 424. That is, the head portion 410 of the periprosthetic ring bone fixation plate 400 may include alternating locking screw openings 422 and variable angled openings 424 in the first and second legs 412, 413. In one embodiment, the bridge segment 414 may include a plurality of variable angle openings 424, alternatively it is envisioned that the bridge segment 414 may also include one or more locking screw openings 422. By providing a plurality of locking screw openings 422 and variable angled openings 424 in the head portion 410 of the periprosthetic ring bone fixation plate 400, a surgeon is provided with increased options as compared to conventional known ring fixation plates.

As illustrated, in one embodiment, an opening 420 (e.g., a variable angle opening 424a) is centrally positioned on the bridge segment 414. Thus arranged, the periprosthetic ring bone fixation plate 400 can be cut as needed. As such, the integrally formed ring-shaped head portion 410 of the periprosthetic ring bone fixation plate 400 can be divided into two arms (e.g., first and second legs 412, 413 can be converted into first and second hook-type members).

In addition, as previously described in connection with the proximal femur bone fixation plate 100, the periprosthetic ring bone fixation plate 400 may include a plurality of locking screw openings 422 and a plurality of variable angled openings 424 in the shaft portion 415 of the periprosthetic ring bone fixation plate 400. Similar to the locking screw openings 122 and variable angled openings 124 described in connection with the proximal femur bone fixation plate 100, and in accordance with one aspect of the present disclosure, the locking screw openings 422 formed in the shaft portion 415 of the periprosthetic ring bone fixation plate 400 may be arranged and configured to receive larger diameter bone fasteners relative to the variable angled openings 424 formed in the shaft portion 415 of the periprosthetic ring bone fixation plate 400. That is, for example, the locking screw openings 422 formed in the shaft portion 415 may be arranged and configured to receive 4.5 mm bone fasteners while the variable angled openings 424 formed in the shaft portion 415 may be arranged and configured to receive 3.5 mm bone fasteners, although these dimensions are merely exemplary and other dimensioned bone fasteners are envisioned. By arranging and configuring the periprosthetic ring bone fixation plate 400 to receive larger diameter locking screws, the periprosthetic ring bone fixation plate

400 is better able to secure to the patient's bone. Meanwhile, by incorporating smaller, variable angled openings 424 in the shaft portion 415, the periprosthetic ring bone fixation plate 400 is better able to facilitate positioning of the non-locking screws (e.g., polyaxial variable angled bone screws) around the previous surgically implanted orthopedic device or implant.

In addition, and/or alternatively, in accordance with another aspect or feature of the present disclosure and as previously described, the locking screw openings 422 positioned within the shaft portion 415 of the periprosthetic ring bone fixation plate 400 may be more centrally located as compared to the variable angled openings 424, which as illustrated, may be positioned along and/or adjacent to an outer periphery or surface 406 of the shaft portion 415 of the periprosthetic ring bone fixation plate 400. For example, in one embodiment, the shaft portion 415 may include a central longitudinal axis $C_L$, the locking screw openings 422 positioned within the shaft portion 415 of the periprosthetic ring bone fixation plate 400 may be substantially centrally located along the central longitudinal axis $C_L$ of the shaft portion 415 of the periprosthetic ring bone fixation plate 400. That is, the locking screw openings 422 are positioned more interior, closer to the central longitudinal axis $C_L$ of the shaft portion 415 relative to the variable angled openings 424, which are positioned closer to the outer periphery or perimeter surface 406 of the shaft portion 415.

Thus arranged, by positioning the variable angled openings 424 along and/or adjacent to the outer periphery or surface 406 of the shaft portion 415, the periprosthetic ring bone fixation plate 400 is better able to position the variable angled bone fastener to avoid the previous surgically implanted orthopedic device or implant (e.g., the surgeon is better able to position and insert one or more bone fastener through the variable angled openings formed in the periprosthetic ring bone fixation plate 400 while avoiding, for example, a stem portion of a hip prosthetic or IM nail of a previous surgically implanted orthopedic device or implant in the patient's femur).

In addition, and/or alternatively, in accordance with another aspect or feature of the present disclosure and as previously described in connection with the periprosthetic proximal femur bone fixation plate 100, the shaft portion 415 of the periprosthetic ring bone fixation plate 400 may include a first region 416 and a second region 418. As illustrated, the first region 416 may be positioned adjacent to the head portion 410 of the periprosthetic ring bone fixation plate 400. In one or more embodiments, the variable angled openings 424 may be arranged and configured so that they are positioned transversely to one another. That is, as illustrated and as previously described, the variable angled openings 424 may be seen as being positioned in transverse rows with two variable angled openings 424 positioned in each row, such as, for example, one on each side surface of the central longitudinal axis $C_L$ of the shaft portion 415 of the periprosthetic ring bone fixation plate 400. Meanwhile, as illustrated, the variable angled openings 424 formed in the second region 418 of the shaft portion 415 of the periprosthetic ring bone fixation plate 400 may be arranged so that they alternate relative to each other. That is, as illustrated, the variable angled openings 424 may be seen as being positioned in transverse rows with only a single variable angled opening 424 positioned in a row, with the variable angled openings 424 alternating which side of the central longitudinal axis $C_L$ of the shaft portion 415 of the periprosthetic ring bone fixation plate 400 it is positioned on. Thus arranged, as illustrated, the first region 416 of the shaft portion 415 may include more (e.g., double) variable angled openings 424 as compared to the second region 418 of the shaft portion 415. By positioning the variable angled openings 424 in double rows in the first region 416 of the shaft portion 415, the surgeon is provided with increased options when inserting bone fasteners into the patient's bone in the expected vicinity of the stem portion or IM nail of the previous surgically implanted orthopedic device or implant. Meanwhile, by providing only single row of alternating variable angled openings 424 in the second region 418 of the shaft portion 415, the strength of the bone fixation plate 400 is better maintained.

Figures 10, 11:
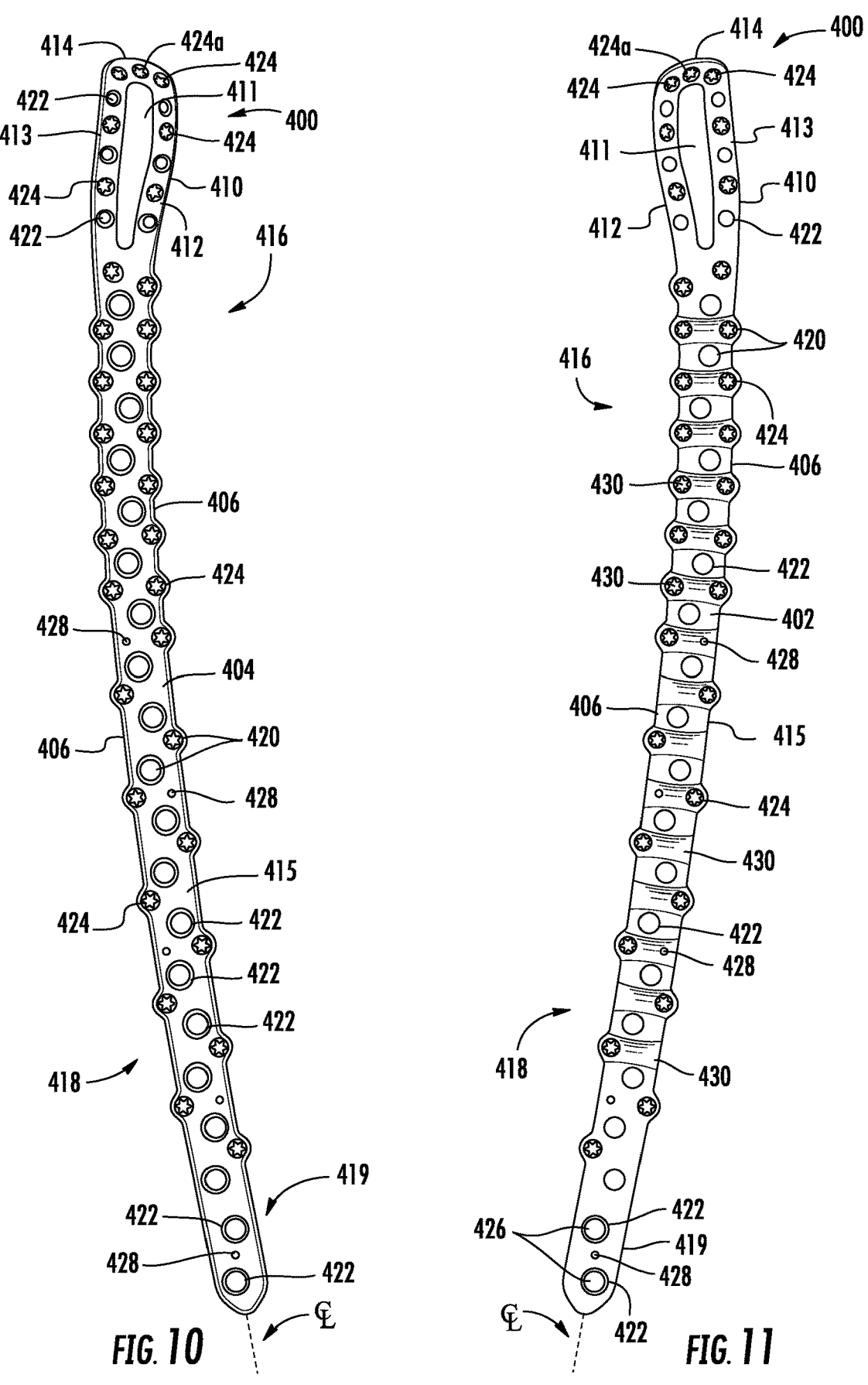
FIG. 10 is a top view of an example embodiment of the bone fixation plate in accordance with the present disclosure.
FIG. 11 is a bottom view of the bone fixation plate shown in FIG. 10.

Referring to FIGS. 11 and 13, the shaft portion 415 of the periprosthetic ring bone fixation plate 400 may include a plurality of undercuts or grooves 430 formed in the underside or bone facing surface 402. However, in addition, and/or alternatively, in accordance with another aspect or feature of the present disclosure and as previously described, the plurality of undercuts 430 may be coincidence with or collocated with the variable angled openings 424 formed in the shaft portion 415 of the periprosthetic ring bone fixation plate 400. That is, the variable angled openings 424 formed in the shaft portion 415 may be positioned or reside within the undercuts 430 formed in the bone facing surface 402. In use, the undercuts 430 may be sized and configured to provide clearance for a cable to pass underneath the periprosthetic ring bone fixation plate 400.

As previously mentioned, in one embodiment, the plurality of undercuts 430 are collocated with the variable angled openings 424 formed in the shaft portion 415 of the periprosthetic ring bone fixation plate 400 to provide increased bone plate strength (e.g., the undercuts 430 and the variable angled openings 424 are centered between the central locking screw openings 422, which is the location of the peak stress. If either the undercuts 430 or the variable angled openings 424 were positioned closer to one of the central locking screw openings 422, the overall strength of the plate would be diminished).

In addition, and/or alternatively, in accordance with another aspect or feature of the present disclosure and as previously described in connection with the periprosthetic proximal femur bone fixation plate 100, the distal end portion 419 of the shaft portion 415 (e.g., an end portion 419 of the plate 400 opposite the head portion 410) of the periprosthetic ring bone fixation plate 400 may include thinning That is, the end portion 419 may include a reduced or tapering cross-sectional area to facilitate contouring of the end portion 419 relative to the patient's anatomy. In accordance with one aspect or feature of the present disclosure, the distal end portion 419 of the shaft portion 415 may incorporate a reduced cross-sectional area to better enable the surgeon to contour the end portion 419 to accommodate the patient's anatomy. For example, as previously mentioned, providing a bone fixation plate anatomically constrained or contoured at both ends will not fit individual patients as intended. Thus, it is beneficial to anatomically un-constrain one end of the bone plate to enable contouring of the bone plate to provide a better fit for each individual patient.

In addition, referring to FIGS. 11 and 13, in accordance with another aspect of the present disclosure and as previously described above in connection with the periprosthetic proximal femur bone fixation plate 100, the locking screw openings 422 formed in the end portion 419 of the plate 400 may include an underside counterbore 426 formed in the underside or bone facing surface 402 thereof. For example, as illustrated, the two distal most locking screw openings 422 formed in the shaft portion 415 of the periprosthetic ring bone fixation plate 400 may include an underside counterbore 426, although it is envisioned that more or less locking screw openings may be counterbored on the underside or bone facing surface. In use, by providing a counterbore 426 in the underside or bone facing surface 402 of the locking screw openings 422 formed in the end portion 419 of the plate 400, the underside counterbored locking screw openings may be used in combination with an instrument to grab and compress the bone fracture.

The shaft portion 415 of the periprosthetic ring bone fixation plate 400 may also include a plurality of K-wire openings 428 for enabling a K-wire to pass therethrough. As illustrated, in addition, and/or alternatively, in accordance with another aspect or feature of the present disclosure, an initial K-wire opening 428 may be positioned between the two distal most locking screw openings 422. In addition, the shaft portion 415 may include a plurality of additional K-wire openings 428 formed in the second region 418 of the shaft portion 415. In use, the plurality of K-wire openings 428 allow a surgeon to provisionally hold the bone fixation plate 400 to the patient's bone after they have reduced the fracture.

As generally shown, and as will be appreciated by one of ordinary skill in the art, the number of undercuts, variable angled openings, locking screw openings, etc. will be variable between the various bone fixation plates depending on the length of the plate.

Periprosthetic Troch Hook Bone Fixation Plate

Figure 14:
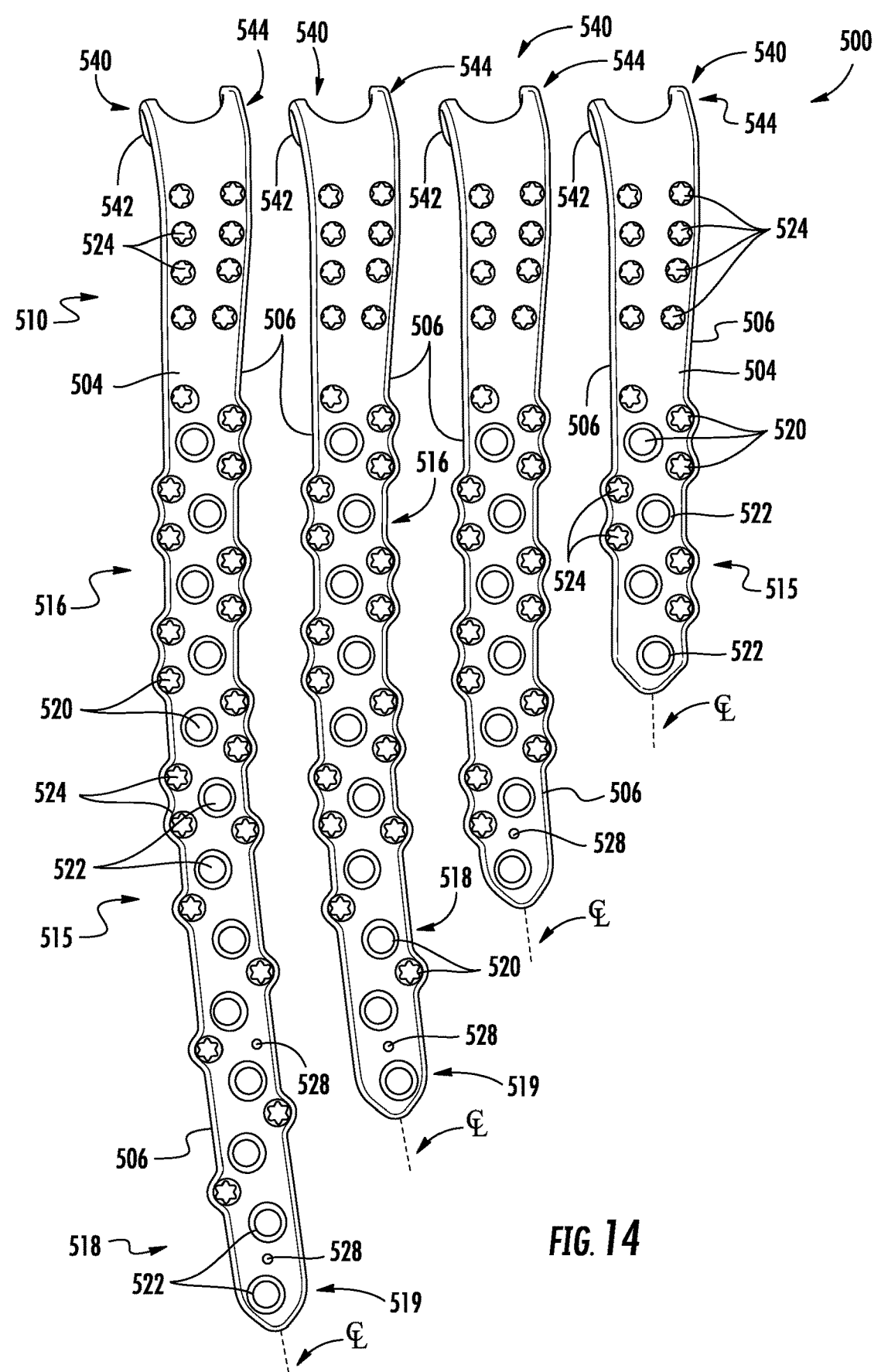
FIG. 14 is a top view of various length bone fixation plates in accordance with the present disclosure.

Referring to FIGS. 14-16, various embodiments of an alternate bone fixation plate 500 having various lengths for repairing fractures in a patient's bone is disclosed. As will be described herein, the bone fixation plates 500 illustrated and described in connection with FIGS. 14-16 may be substantially similar to the periprosthetic proximal femur bone fixation plate 100 described above in connection with FIGS. 1-3B, however the bone fixation plate 500 may be in the form of a hook plate. That is, the bone fixation plate 500 includes a head portion 510 incorporating hook members 540 (e.g., first and second hook members 542, 544) arranged and configured for engaging the trochanter of a patient. In addition, as will be described herein, the bone fixation plate 500 includes one or more features so that the bone fixation plate 500 facilitates positioning and securement to a patient's bone such as, for example, a patient's femur, which previously received a surgically implanted orthopedic implant or device such as, for example, an IM nail, a hip prosthetic, etc. As such, the bone fixation plate 500 is arranged and configured for periprosthetic fractures and thus may be referred to as a periprosthetic bone fixation plate or periprosthetic troch hook bone fixation plate.

As shown, the periprosthetic troch hook bone fixation plate 500 may include an underside, lower, or bone facing surface 502 and an upper surface 504. In addition, the periprosthetic troch hook bone fixation plate 500 includes a head portion 510 and a shaft portion 515. Moreover, the periprosthetic troch hook bone fixation plate 500 includes a plurality of openings 520 formed therein for receiving a plurality of fasteners (not shown) for coupling the periprosthetic troch hook bone fixation plate 500 to the patient's bone.

As shown, the head portion 510 of the periprosthetic troch hook bone fixation plate 500 includes hook members 540 (e.g., first and second hook members 542, 544) arranged and configured for engaging a patient's trochanter. That is, as shown, the periprosthetic troch hook bone fixation plate 500 includes first and second hook members 542, 544 extending from the head portion 510 thereof (e.g., extending from the proximal end of the head portion 510). In accordance with one aspect of the present disclosure, in contrast to known hook plates, the periprosthetic troch hook bone fixation plate 500 includes first and second hook members 542, 544 that are asymmetrical. That is, the first hook member 542 is different than the second hook member 544. For example, the first hook member 542 may have a different size and/or configuration as compared to the second hook member 544. By incorporating asymmetrical hook members 540, the periprosthetic troch hook bone fixation plate 500 is better able to match the anatomic slant of a patient's trochanter.

In addition, and/or alternatively, in accordance with another aspect or feature of the present disclosure, the head portion 510 of the periprosthetic troch hook bone fixation plate 500 may include a plurality of variable angled openings 524. That is, the head portion 510 of the periprosthetic troch hook bone fixation plate 500 may be devoid of any locking screw openings 522 (as best shown in FIG. 14), although it is envisioned that in some embodiments, locking screw openings may also be incorporated. As shown, for example, the variable angled openings 524 formed in the head portion 510 may be arranged in an array such as, for example, a 2×4 array, although this is merely exemplary and other arrays and/or configurations are envisioned. By providing an array of variable angled openings 524 in the head portion 510, a surgeon is provided with increased options for positioning variable angled bone fasteners into the patient's bone.

In addition, as previously described in connection with the proximal femur bone fixation plate 100, the periprosthetic troch hook bone fixation plate 500 may include a plurality of locking screw openings 522 and a plurality of variable angled openings 524 in the shaft portion 515 of the periprosthetic troch hook bone fixation plate 500. Similar to the locking screw openings 122 and variable angled openings 124 described in connection with the proximal femur bone fixation plate 100, and in accordance with one aspect of the present disclosure, the locking screw openings 522 formed in the periprosthetic troch hook bone fixation plate 500 may be arranged and configured to receive larger diameter bone fasteners relative to the variable angled openings 524 formed in the periprosthetic troch hook bone fixation plate 500. That is, for example, the locking screw openings 522 may be arranged and configured to receive 4.5 mm bone fasteners while the variable angled openings 524 may be arranged and configured to receive 3.5 mm bone fasteners, although these dimensions are merely exemplary and other dimensioned bone fasteners are envisioned. By arranging and configuring the periprosthetic troch hook bone fixation plate 500 to receive larger diameter locking screws, the periprosthetic troch hook bone fixation plate 500 is better able to secure to the patient's bone. Meanwhile, by incorporating smaller, variable angled openings 524, the periprosthetic troch hook bone fixation plate 500 is better able to facilitate positioning of the non-locking screws (e.g., polyaxial variable angled bone screws) around the previous surgically implanted orthopedic device or implant.

In addition, and/or alternatively, in accordance with another aspect or feature of the present disclosure and as previously described, the locking screw openings 522 may be positioned within the shaft portion 515 of the periprosthetic troch hook bone fixation plate 500 more centrally as compared to the variable angled openings 524. For example, in one embodiment, the shaft portion 515 may include a central longitudinal axis $C_L$, the locking screw openings 522 may be positioned within the shaft portion 515 of the periprosthetic troch hook bone fixation plate 500 more centrally, substantially along the central longitudinal axis $C_L$, as compared to the variable angled openings 524, which as illustrated, may be positioned along and/or adjacent to an outer periphery or surface 506 of the shaft portion 515 of the periprosthetic troch hook bone fixation plate 500. That is, the locking screw openings 522 are positioned more interior, closer to the central longitudinal axis $C_L$ of the shaft portion 515 relative to the variable angled openings 524, which are positioned closer to the outer periphery or perimeter surface 506 of the shaft portion 515.

Thus arranged, by positioning the variable angled openings 524 along and/or adjacent to the outer periphery or surface 506 of the shaft portion 515, the periprosthetic troch hook bone fixation plate 500 is better able to position the variable angled bone fastener to avoid the previous surgically implanted orthopedic device or implant (e.g., the surgeon is better able to position and insert one or more bone fastener through the variable angled openings 524 formed in the periprosthetic troch hook bone fixation plate 500 while avoiding, for example, a stem portion of a hip prosthetic or IM nail of a previous surgically implanted orthopedic device or implant in the patient's femur).

In addition, and/or alternatively, in accordance with another aspect or feature of the present disclosure and as previously described in connection with the periprosthetic proximal femur bone fixation plate 100, the shaft portion 515 of the periprosthetic troch hook bone fixation plate 500 may include a first region 516 and a second region 518. As illustrated, the first region 516 may be positioned adjacent to the head portion 510 of the periprosthetic troch hook bone fixation plate 500. In one or more embodiments, as shown in FIG. 14, in the first region 516 of the shaft portion 515, the variable angled openings 524 may be arranged and configured so that there are multiple variable angled openings 524 positioned on one side of the locking screw opening 522 with the position of the variable angled openings 524 alternating sides with every locking screw opening 522. Thereafter, as illustrated, the variable angled openings 524 formed in the second region 518 of the shaft portion 515 of the periprosthetic troch hook bone fixation plate 500 may be arranged with a single variable angled opening 524 for each locking screw opening 522. In use, as compared to, for example, the periprosthetic ring bone fixation plate 400, the width of the periprosthetic troch hook bone fixation plate 500 may be less. In addition, the periprosthetic troch hook bone fixation plate 500 may be loaded during insertion. As such, the variable angled openings 524 in the shaft portion 515 are arranged and configured to be as spread out (e.g., across the width of the shaft portion 515) as possible. Thus arranged, as illustrated, the first region 516 of the shaft portion 515 may include more (e.g., double) variable angled openings 524 as compared to the second region 518 of the shaft portion 515 thereby providing the surgeon with increased options when inserting bone fasteners into the patient's bone in the expected vicinity of the stem portion or IM nail of the previous surgically implanted orthopedic device or implant.

In addition, and/or alternatively, although not shown, it is envisioned that the shaft portion 515 of the periprosthetic troch hook bone fixation plate 500 may include a plurality of undercuts or grooves formed in the underside or bone facing surface 502. In use, the undercuts may be sized and configured to provide clearance for a cable to pass underneath the periprosthetic troch hook bone fixation plate 500.

In addition, and/or alternatively, in accordance with another aspect or feature of the present disclosure and as previously described in connection with the periprosthetic proximal femur bone fixation plate 100, an end portion 519 of the periprosthetic troch hook bone fixation plate 500 (e.g., the end portion 519 of the plate 500 opposite the head portion 510) may include thinning That is, the end portion 519 may include a reduced or tapering cross-sectional area to facilitate contouring of the end portion 519 relative to the patient's anatomy. In accordance with one aspect or feature of the present disclosure, the end portion 519 may incorporate a reduced cross-sectional area to better enable the surgeon to contour the end portion 519 to accommodate the patient's anatomy. For example, as previously mentioned, providing a bone fixation plate with both ends contoured creates numerous issues. For example, generally speaking, providing a bone fixation plate anatomically constrained or countered at both ends will not fit individual patients as intended. Thus, it is beneficial to anatomically un-constrain one end of the bone plate to enable contouring of the bone plate to provide a better fit for each individual patient. In accordance with one aspect or feature of the present disclosure, the end portion 519 (e.g., end portion opposite the head portion 510) may incorporate a reduced cross-sectional area to better enable the surgeon to contour the end portion 519 to accommodate the patient's anatomy.

In addition, referring to FIGS. 15 and 16, in accordance with another aspect of the present disclosure and as previously described above in connection with the proximal femur bone fixation plate 100, the locking screw openings 522 formed in the end portion 519 may include an underside counterbore 526 formed in the underside or bone facing surface 502 thereof. For example, as illustrated, the two distal most locking screw openings 522 formed in the shaft portion 515 of the periprosthetic troch hook bone fixation plate 500 may include an underside counterbore, although it is envisioned that more or less locking screw openings may be counterbored on the underside or bone facing surface. In use, by providing a counterbore in the underside of the locking screw openings formed in the distal end portion of the plate, the underside counterbored locking screw openings may be used in combination with an instrument to grab and compress the bone fracture.

The shaft portion of the periprosthetic troch hook bone fixation plate 500 may also include a plurality of K-wire openings 528 for enabling a K-wire to pass therethrough. As illustrated, in addition, and/or alternatively, in accordance with another aspect or feature of the present disclosure, an initial K-wire opening 528 may be positioned between the two distal most locking screw openings 522. In addition, the shaft portion 515 may include a plurality of additional K-wire openings 528 formed therein. In use, the plurality of K-wire openings 528 allow a surgeon to provisionally hold the bone fixation plate 500 to the patient's bone after they have reduced the fracture.

As generally shown, and as will be appreciated by one of ordinary skill in the art, the number of undercuts, variable angled openings, locking screw openings, etc. will be variable between the various bone fixation plates depending on the length of the plate.

The foregoing description has broad application. Accordingly, the discussion of any embodiment is meant only to be explanatory and is not intended to suggest that the scope of the disclosure, including the claims, is limited to these example embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The term "a" or "an" entity, as used herein, refers to one or more of that entity. As such, the terms "a" (or "an"), "one or more" and "at least one" can be used interchangeably herein. The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein. The phrases "at least one", "one or more", and "and/or", as used herein, are open-ended expressions that are both conjunctive and disjunctive in operation.

All directional references (e.g., proximal, distal, upper, underside, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another. The drawings are for purposes of illustration only and the dimensions, positions, order and relative sizes reflected in the drawings attached hereto may vary.

We claims:

1. A periprosthetic bone plate comprising:

a head portion; and a shaft portion including an upper surface, a lower surface, a central longitudinal axis, and an outer periphery surface, the shaft portion further including:

a plurality of threaded locking screw openings arranged and configured to receive a plurality of locking screws, respectively, for securing the bone plate to a patient's bone; and a plurality of variable angled fastener openings arranged and configured to receive a plurality of variable angled screws, respectively, for securing the bone plate to the patient's bone;

wherein the plurality of variable angled fastener openings are positioned along the outer periphery surface of the shaft portion while the plurality of locking screw openings are positioned closer to the central longitudinal axis of the shaft portion; and wherein the plurality of variable angled fastener openings and the plurality of locking screw openings form a plurality of groups, each of the plurality of groups comprising a triangular configuration on the upper surface of the bone plate such that a locking screw opening of the plurality of locking screw openings is positioned in-between adjacent variable angled fastener openings on two of the three sides of each of the triangular configurations.

2. The periprosthetic bone plate of claim 1, wherein the plurality of threaded locking screw openings include a first diameter and the plurality of variable angled fastener openings include a second diameter, the first diameter being larger than the second diameter.

3. The periprosthetic bone plate of claim 1, further comprising a plurality of undercuts formed in the lower surface of the shaft portion of the bone plate, the plurality of undercuts extending laterally from a first lateral side to a second lateral side of the bone plate, the plurality of undercuts being coincident with the plurality of variable angled fastener openings so that a variable angled fastener opening is positioned within one of the plurality of undercuts.

4. The periprosthetic bone plate of claim 1, wherein an end portion of the shaft portion, opposite the head portion, includes thinning so that the end portion of the shaft portion includes a tapering cross-sectional area extending from the end portion towards the head portion, the tapering cross-sectional area being arranged and configured to enable contouring of the end portion of the shaft portion.

5. The periprosthetic bone plate of claim 4, wherein the plurality of locking screw openings formed in the end portion of the shaft portion include first and second distal locking screw openings, each of the first and second distal locking screw openings including a counterbore formed in the lower surface of the bone plate.

6. The periprosthetic bone plate of claim 5, further comprising one or more K-wire openings arranged and configured to enable a K-wire to pass therethrough, at least one of the one or more K-wire openings is positioned between the first and second distal locking screw openings.

7. The periprosthetic bone plate of claim 1, wherein the head portion of the periprosthetic bone plate includes a plurality of variable angled fastener openings and is devoid of any locking screw openings.

8. The periprosthetic bone plate of claim 1, wherein the head portion includes a plurality of locking screw openings and a plurality of variable angled fastener openings, the plurality of locking screw openings are more centrally located as compared to the plurality of the variable angled fastener openings.

9. The periprosthetic bone plate of claim 1, wherein the periprosthetic bone plate is selected from one of a proximal femur plate, a distal femur plate, a periprosthetic ring plate, a periprosthetic hook plate, and a humerus plate.

10. A periprosthetic bone plate comprising:

a head portion; and a shaft portion including an upper surface, a lower surface, a central longitudinal axis, and an outer periphery surface, the shaft portion further including:

a plurality of threaded locking screw openings arranged and configured to receive a plurality of locking screws, respectively, for securing the bone plate to a patient's bone; and a plurality of variable angled fastener openings arranged and configured to receive a plurality of variable angled screws, respectively, for securing the bone plate to the patient's bone;

wherein the plurality of variable angled fastener openings are positioned along the outer periphery surface of the shaft portion while the plurality of locking screw openings are positioned closer to the central longitudinal axis of the shaft portion; and wherein the plurality of variable angled fastener openings and the locking screw openings define a zig-zag forming a line extending along a length of the shaft portion such that a locking screw opening of the plurality of locking screw openings is positioned in-between each pair of adjacent variable angled fastener openings along the zig-zag line.

11. The periprosthetic bone plate of claim 10, wherein the plurality of threaded locking screw openings include a first diameter and the plurality of variable angled fastener openings include a second diameter, the first diameter being larger than the second diameter.

12. The periprosthetic bone plate of claim 10, further comprising a plurality of undercuts formed in the lower surface of the shaft portion of the bone plate, the plurality of undercuts extending laterally from a first lateral side to a second lateral side of the bone plate, the plurality of undercuts being coincident with the plurality of variable angled fastener openings so that a variable angled fastener opening is positioned within one of the plurality of undercuts.

13. The periprosthetic bone plate of claim 10, wherein an end portion of the shaft portion, opposite the head portion, includes thinning so that the end portion of the shaft portion includes a tapering cross-sectional area extending from the end portion towards the head portion, the tapering cross-sectional area being arranged and configured to enable contouring of the end portion of the shaft portion.

14. The periprosthetic bone plate of claim 13, wherein the plurality of locking screw openings formed in the end portion of the shaft portion include first and second distal locking screw openings, each of the first and second distal locking screw openings including a counterbore formed in the lower surface of the bone plate.

15. The periprosthetic bone plate of claim 14, further comprising one or more K-wire openings arranged and configured to enable a K-wire to pass therethrough, at least one of the one or more K-wire openings is positioned between the first and second distal locking screw openings.

\* \* \* \* \*